(12) United States Patent
Kavita et al.

(10) Patent No.: US 12,312,395 B2
(45) Date of Patent: May 27, 2025

(54) METHODS OF AAV THERAPY

(71) Applicant: Bristol-Myers Squibb Company, Princeton, NJ (US)

(72) Inventors: Uma Kavita, Princeton, NJ (US); Yanshan Dai, Princeton, NJ (US); Lisa Salvador, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1192 days.

(21) Appl. No.: 17/254,191

(22) PCT Filed: Jun. 19, 2019

(86) PCT No.: PCT/US2019/037949
§ 371 (c)(1),
(2) Date: Dec. 18, 2020

(87) PCT Pub. No.: WO2019/246237
PCT Pub. Date: Dec. 26, 2019

(65) Prior Publication Data
US 2021/0122807 A1 Apr. 29, 2021

Related U.S. Application Data

(60) Provisional application No. 62/687,564, filed on Jun. 20, 2018.

(51) Int. Cl.
*A61K 48/00* (2006.01)
*C07K 16/08* (2006.01)
*G01N 33/543* (2006.01)
*G01N 33/68* (2006.01)

(52) U.S. Cl.
CPC ......... *C07K 16/081* (2013.01); *G01N 33/543* (2013.01); *G01N 33/6857* (2013.01); *G01N 2333/075* (2013.01); *G01N 2469/20* (2013.01)

(58) Field of Classification Search
None
See application file for complete search history.

(56) References Cited

U.S. PATENT DOCUMENTS

2013/0273579 A1 10/2013 Sawasaki et al.

FOREIGN PATENT DOCUMENTS

| WO | WO-2012067165 A1 | 5/2012 |
| WO | WO-2016172608 A1 | 10/2016 |
| WO | WO-2017096162 A1 | 6/2017 |
| WO | WO-2019246237 A1 | 12/2019 |

OTHER PUBLICATIONS

Xiao (Journal of Virology, 1999, Vo. 73, No. 5, pp. 3994-4003). (Year: 1999).*

Samaranch, L., et al., "MR-guided parenchymal delivery of adeno-associated viral vector serotype 5 in on-human primate brain," *Gene Therapy* 24(4):253-61 (Mar. 2017).
Amine, M.A. and Anand, V., "Anatomy and Complications: Safe Sinus," Otolaryngologic Clinics of North America 48(5):739-748, W B Saunders, United States (Oct. 2015).
Atchison, R.W., et al., "Adenovirus-Associated Defective Virus Particles," Science 149(3685):754-756, American Association for the Advancement of Science, United States (Aug. 1965).
Blacklow, N.R., et al., "Serologic Evidence for Human Infection With Adenovirus-associated Viruses," Journal of the National Cancer Institute 40(2):319-327, Oxford University Press, United States (Feb. 1968).
Boutin, S., et al., "Prevalence of Serum IgG and Neutralizing Factors Against Adeno-associated Virus (AAV) Types 1, 2, 5, 6, 8, and 9 in the Healthy Population: Implications for Gene Therapy Using AAV Vectors," Human Gene Therapy 21(6):704-712, Liebert, United States (Jun. 2010).
Calcedo., R., et al., "Adeno-associated virus antibody profiles in newborns, children, and adolescents," Clin. Vaccine Immunol. 18(9):1586-1588, American Society for Microbiology, United States (Sep. 2011).
Calcedo, R., et al., "Host immune responses to chronic adenovirus infections in human and nonhuman primates," J. Virol. 83(60):2623-2631 American Society for Microbiology, United States (Mar. 2009).
Cheung, A.K., et al., "Integration of the Adeno-associated Virus Genome Into Cellular DNA in Latently Infected Human Detroit 6 Cells," Journal of Virology 33(2):739-748, American Society For Microbiology, United States (Feb. 1980).
Chirmule, N., et al., "Immune Responses to Adenovirus and Adeno-associated Virus in Humans," Gene Therapy 6(9):1574-1583, Nature Publishing Group, England (Sep. 1999).
Deng, W.P. and Nickoloff, J.A., "Site-directed Mutagenesis of Virtually Any Plasmid by Eliminating a Unique Site," Analytical Biochemistry 200(1):81-88, Elsevier, United States (Jan. 1992).
Erles, K., et al., "Update on the Prevalence of Serum Antibodies (IgG and IgM) to Adeno-associated Virus (AAV)," Journal of Medical Virology 59(3):406-411, Wiley-Liss, United States (Nov. 1999).
Falese, L., et al., "Strategy to Detect Pre-existing Immunity to AAV Gene Therapy," Gene Therapy 24(12):768-778, Nature Publishing Group, England (Dec. 2017).
Veron, P., et al. "Humoral and cellular capsid-specific immune responses to adeno-associated virus type 1 in randomized healthy donors." Journal of immunology (Baltimore, Md. : 1950) vol. 188,12 (Jun. 2012).

(Continued)

*Primary Examiner* — Celine X Qian
(74) *Attorney, Agent, or Firm* — Sterne, Kessler, Goldstein & Fox P.L.L.C.

(57) ABSTRACT

This disclosure provides methods for identifying a subject suitable for an adeno associated vims (AAV) therapy. In some embodiments, the method comprises measuring a titer of an antibody or antigen-binding portion thereof that specifically binds to an AAV ("anti-AAV antibody") in a biological sample obtained from the subject using an enzyme-linked immunosorbent assay (ELISA).

12 Claims, 18 Drawing Sheets

(56) References Cited

OTHER PUBLICATIONS

Xiao, X., et al., "Production of High-titer Recombinant Adeno-associated Virus Vectors in the Absence of Helper Adenovirus," Journal of Virology 72(3):2224-2232, American Society For Microbiology, United States (Mar. 1998).

Gao, G., et al., "Clades of Adeno-associated Viruses are Widely Disseminated in Human Tissues," Journal of Virology 78(12):6381-6388, American Society For Microbiology, United States (Jun. 2004).

Calcedo, R., et al., "Worldwide epidemiology of neutralizing antibodies to adeno-associated viruses," J. Infect. Dis. 199(3):381-390, Oxford Academic Press, United Kingdom (Jan. 2009).

Goncalves, M.A.F.V., "Adeno-associated Virus: From Defective Virus to Effective Vector," Virology Journal 2:43, BioMed Central, England (May 2005).

Gottlieb, J. and Muzyczka, N., "In Vitro Excision of Adeno-Associated Virus DNA from Recombinant Plasmids: Isolation of an Enzyme Fraction from HeLa Cells That Cleaves DNA at Poly(G) Sequences," Molecular and Cellular Biology 8(6):2513-2522, American Society for Microbiology, United States (Jun. 1988).

Hermonat, P.L. and Muzyczka, N., "Use of Adeno-Associated Virus as a Mammalian DNA Cloning Vector: Transduction of Neomycin Resistance into Mammalian Tissue Culture Cells," Proceedings of the National Academy of Sciences of the United States of America 81(20):6466-6470, National Academy of Sciences, United States (Oct. 1984).

International Search Report and Written Opinion for International Application No. PCT/US2019/037949, European Patent Office, Netherlands, mailed on Sep. 19, 2019, 12 pages.

Kavita, U., et al., "Development of a Chemiluminescent ELISA Method for the Detection of Total Anti-Adeno Associated Virus Serotype 9 (AAV9) Antibodies," Human Gene Therapy Methods 29(6):237-250, Mary Ann Liebert, United States (Dec. 2018).

Keeler, A.M., et al., "Systemic Delivery of AAVB1-GAA Clears Glycogen and Prolongs Survival in a Mouse Model of Pompe Disease," Human Gene Therapy 30(1):57-68, M.A. Liebert, United States (Jan. 2019).

Laughlin, C.A., et al., "Cloning of Infectious Adeno-Associated Virus Genomes in Bacterial Plasmids," Gene 23(1):65-73, Elsevier/North-Holland, Netherlands (Jul. 1983).

Liu, F., et al., "Dynamic Interpretation of Maternal Inputs by the Drosophila Segmentation Gene Network," Proceedings of the National Academy of Sciences of the United States of America 110(17):6724-6729, National Academy of Sciences, United States (Apr. 2013).

Majowicz, S.E., et al., "Global Incidence of Human Shiga Toxin-producing *Escherichia coli* Infections and Deaths: A Systematic Review and Knowledge Synthesis," Foodborne Pathogens and Disease 11(6):447-455, Mary Ann Liebert, Inc., United States (Jun. 2014).

Manno, C.S., et al., "Successful Transduction of Liver in Hemophilia by AAV-Factor IX and Limitations Imposed by the Host Immune Response," Nature Medicine 12(3):342-347, Nature Publishing Company, United States (Mar. 2006).

Martino, A.T., et al., "Measuring Immune Responses to Recombinant AAV Gene Transfer," Methods in Molecular Biology 807:259-272, Humana Press, United States (Sep. 2011).

Masat, E., et al., "Humoral Immunity to AAV Vectors in Gene Therapy: Challenges and Potential Solutions," Discovery Medicine 15(85):379-389, Discovery Medicine, United States (Jun. 2013).

Matsushita, T., et al., "Adeno-associated Virus Vectors can be Efficiently Produced without Helper Virus," Gene Therapy 5(7):938-945, Nature Publishing Group, England (Jul. 1998).

McLaughlin, S.K., et al., "Adeno-associated Virus General Transduction Vectors: Analysis of Proviral Structures," Journal of Virology 62(6):1963-1973, American Society for Microbiology, United States (Jun. 1988).

Meliani, A., et al., "Determination of Anti-adeno-associated Virus Vector Neutralizing Antibody Titer With an in Vitro Reporter System," Human Gene Therapy Methods 26(2):45-53, Mary Ann Liebert, United States (Apr. 2015).

Mingozzi, F., et al., "Pharmacological Modulation of Humoral Immunity in a Nonhuman Primate Model of AAV Gene Transfer for Hemophilia B," Molecular Therapy 20(7):1410-1416, Cell Press, United States (Jul. 2012).

Mori, S., et al., "Two Novel Adeno-associated Viruses From Cynomolgus Monkey: Pseudotyping Characterization of Capsid Protein," Virology 330(2):375-383, Academic Press, United States (Dec. 2004).

Nathwani, A.C., et al., "Long-term Safety and Efficacy of Factor IX Gene Therapy in Hemophilia B," The New England Journal of Medicine 371(21):1994-2004, Massachusetts Medical Society, United States (Nov. 2014).

Rose, J.A., et al., "Evidence for a Single-stranded Adenovirus-associated Virus Genome: Formation of a DNA Density Hybrid on Release of Viral DNA," Proceedings of the National Academy of Sciences of the United States of America 64(3):863-869, National Academy of Sciences, United States (Nov. 1969).

Samulski, R.J., et al., "A Recombinant Plasmid From Which an Infectious Adeno-associated Virus Genome Can Be Excised in Vitro and Its Use to Study Viral Replication," Journal of Virology 61(10):3096-3101, American Society For Microbiology, United States (Oct. 1987).

Samulski, R.J., et al., "Helper-Free Stocks of Recombinant Adeno-Associated Viruses: Normal Integration Does Not Require Viral Gene Expression," Journal of Virology 63(9):3822-3828, American Society For Microbiology, United States (Sep. 1989).

Samulski, R.J., et al., "Rescue of Adeno-associated Virus From Recombinant Plasmids: Gene Correction Within the Terminal Repeats of AAV," Cell 33(1):135-143, Cell Press, United States (May 1983).

Senapathy, P., et al., "Replication of Adeno-associated Virus DNA. Complementation of Naturally Occurring Rep-Mutants by a Wild-type Genome or an Ori-Mutant and Correction of Terminal Palindrome Deletions," Journal of Molecular Biology 179(1):1-20, Elsevier, Netherlands (Oct. 1984).

Takebe, Y., et al., "SR Alpha Promoter: An Efficient and Versatile Mammalian Cdna Expression System Composed of the Simian Virus 40 Early Promoter and the R-U5 Segment of Human T-Cell Leukemia Virus Type 1 Long Terminal Repeat," Molecular and Cell Biology 8(1):466-472, American Society for Microbiology, United States (Jan. 1988).

Tellez, J., et al., "Characterization of Naturally-occurring Humoral Immunity to AAV in Sheep," PloS One 8(9):e75142, Public Library of Science, United States (Sep. 2013).

Thwaite, R., et al., "AAVrh. 10 Immunogenicity in Mice and Humans. Relevance of Antibody Cross-reactivity in Human Gene Therapy," Gene Therapy 22(2):196-201, Nature Publishing Group, England (Feb. 2015).

Valdmanis, P.N., et al., "miR-122 Removal in the Liver Activates Imprinted MicroRNAs and Enables More Effective MicroRNA-mediated Gene Repression," Nature Communications 9(1):5321, Nature Publishing Group, England (Dec. 2018).

Vandamme, C., et al., "Unraveling the Complex Story of Immune Responses to AAV Vectors Trial After Trial," Human Gene Therapy 28(11):1061-1074, Mary Ann Liebert, Inc., United States (Aug. 2017).

Schulz, M., et al., "Binding and neutralizing anti-AAV antibodies: Detection and implications for rAAV-mediated gene therapy," Mol. Ther. 31(3):616-630 (Jan. 2023).

\* cited by examiner

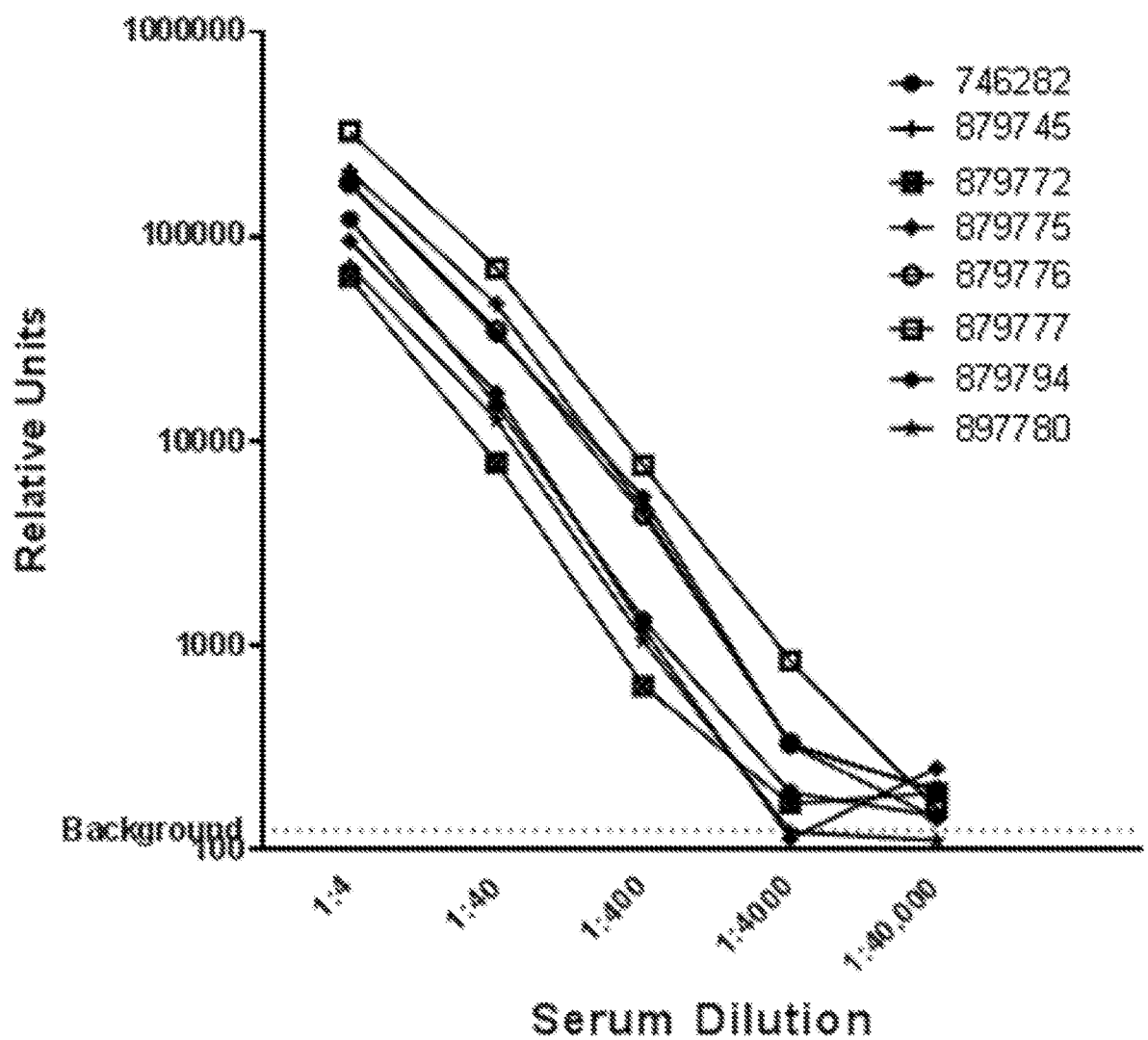

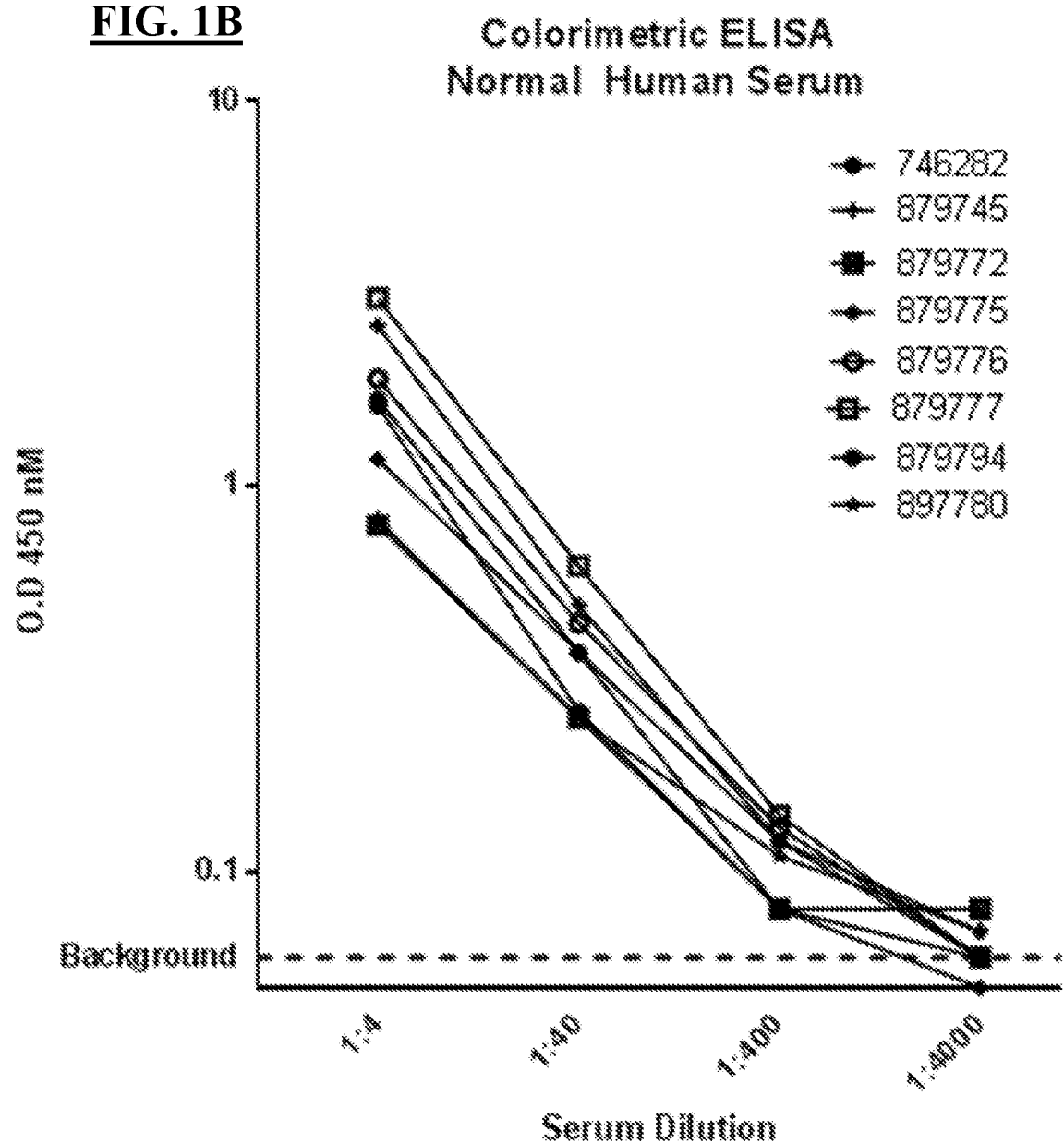

METHODS OF AAV THERAPY

This application claims the benefit of U.S. Provisional Application No. 62/687,564, filed Jun. 20, 2018, which is incorporated by reference herein in its entirety.

FIELD OF THE DISCLOSURE

This disclosure relates to methods for treating a disease in a subject using an adeno associated virus (AAV) therapy. In certain aspects, the methods comprise identifying a patient suitable for an AAV therapy by detecting the total level of anti-AAV antibodies in the subject, and administering to a subject that has a low anti-AAV antibody titer an AAV therapy.

BACKGROUND OF THE DISCLOSURE

Transgene carrying adeno associated viruses (AAV) are an important tool in gene therapy for the correction of genetic deficiencies that result in mutant or null protein expression or for the enhancement of existing low level protein expression (Nathwani et al to A. M Keeler et. al) and potentially for gene knockdown, genome editing or modification, and non-coding RNA modulation (Valdmanis et. al 2017). However, humans become exposed to AAV very early in life and develop anti-AAV antibodies (Blacklow et al., 1967; Boutin et al., 2010; Calcedo et al., 2009, 2011; Liu et al., 2013), including neutralizing anti-AAV antibodies, which can negatively impact gene therapeutic drug efficacy by neutralizing AAV vectors.

Pre-screening and exclusion of patients with high levels of pre-existing neutralizing AAV-specific antibodies is one way of achieving higher drug efficacy. In vitro cell-based reporter assays are most often employed to determine the frequency of neutralizing antibodies in a given population and to exclude patients that may be less likely to respond to an AAV therapy (Amine M et. al., 2015, Manno C et. al., 2006). However, cell-based neutralizing antibody assays are low throughput and labor intensive and, in general, suffer from high variability and low sensitivity issues, making it difficult to screen samples from large numbers of patients. Accordingly, there remains a need in the art to develop methods that provide information about the presence of pre-existing antibodies that are less variable and more robust, and for methods that are more amendable for high-throughput and automation that can potentially be used to screen large numbers of subjects for patient exclusion purposes.

SUMMARY OF THE DISCLOSURE

In certain aspects, the present disclosure is directed to a method of identifying a subject suitable for an adeno associated virus (AAV) therapy, comprising measuring a titer of an antibody or antigen-binding portion thereof that specifically binds to an AAV ("anti-AAV antibody") in a biological sample obtained from the subject using an enzyme-linked immunosorbent assay (ELISA). In some embodiments, the method further comprises administering an AAV therapy to a subject identified as having a low titer of the anti-AAV antibody.

In certain aspects, the present disclosure is directed to a method of treating a disease in a subject, comprising administering to the subject an AAV therapy, wherein the subject is identified as having a low titer of an anti-AAV antibody as measured using a biological sample obtained from the subject in an ELISA.

In certain aspects, the present disclosure is directed to an AAV therapy for use in treating a disease in a subject, wherein the subject is identified as having a low titer of an anti-AAV antibody as measured using a biological sample obtained from the subject in an ELISA.

In certain aspects, the present disclosure is directed to a method of treating a disease in a subject, comprising (1) measuring the titer of an anti-AAV antibody in a biological sample obtained from the subject in an ELISA, wherein the subject is identified as having a low titer of an anti-AAV antibody and (2) administering to the subject identified as having a low titer of an anti-AAV antibody an AAV therapy.

In certain aspects, the present disclosure is directed to an AAV therapy for use in treating a disease in a subject, wherein a titer of an anti-AAV antibody in a biological sample obtained from the subject is measured in an ELISA, and wherein the subject who is identified as having a low titer of an anti-AAV antibody is to be administered the AAV therapy.

In certain aspects, the present disclosure is directed to a method of treating a disease in a subject, comprising (1) obtaining a biological sample from the subject, (2) measuring the titer of an anti-AAV antibody in the biological sample in an ELISA, wherein the subject is identified as having a low titer of an anti-AAV antibody, and (3) administering to the subject identified as having a low titer of an anti-AAV antibody an AAV therapy.

In certain aspects, the present disclosure is directed to an AAV therapy for use in treating a disease in a subject, wherein a titer of an anti-AAV antibody in a biological sample obtained from a subject is measured in an ELISA, and wherein the subject who is identified as having a low titer of an anti-AAV antibody is to be administered the AAV therapy.

In some embodiments, the disease is in the heart, liver, lungs, eyes, blood, nervous system, lymphatic system, muscle, stem cells or any combination thereof. In some embodiments, the disease is a heart disease.

In certain aspects, the present disclosure is directed to a high-throughput method of identifying subjects suitable for adeno associated virus (AAV) therapy, comprising measuring a titer of an antibody or antigen-binding portion thereof that specifically binds to an AAV ("anti-AAV antibody") in each of a plurality of biological samples obtained from a corresponding plurality of subjects using an ELISA. In some embodiments, the plurality of subjects comprises about 5 to about 10, about 10 to about 20, about 30 to about 40, or about 40 to about 50 subjects. In some embodiments, the titer in each of the plurality of biological samples is measured in parallel or sequentially.

In some embodiments, the titer of an anti-AAV antibody includes a titer of a neutralizing anti-AAV antibody, a titer of a non-neutralizing anti-AAV-antibody, or both. In some embodiments, the ELISA comprises a secondary antibody that binds to the neutralizing anti-AAV antibody or the non-neutralizing anti-AAV-antibody. In some embodiments, the ELISA comprises a secondary antibody that binds to the neutralizing anti-AAV antibody and the non-neutralizing anti-AAV-antibody.

In some embodiments, the AAV therapy comprises administering a recombinant AAV. In some embodiments, the AAV therapy comprises administering an AAV selected from the group consisting of AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any combination thereof. In some embodiments, the AAV therapy comprises administering an AAV type 5. In some embodiments, the AAV therapy comprises administering an AAV type 9. In some embodiments, the AAV therapy comprises administering an AAV type 2.

In some embodiments, the anti-AAV antibody is an anti-AAV type 1 antibody, anti-AAV type 2 antibody, anti-AAV type 3A antibody, anti-AAV type 3B antibody, anti-AAV type 4 antibody, anti-AAV type 5 antibody, anti-AAV type 6 antibody, anti-AAV type 7 antibody, anti-AAV type 8 antibody, anti-AAV type 9 antibody, anti-AAV type 10 antibody, anti-AAV type 11 antibody, anti-AAV type 12 antibody, anti-AAV type 13 antibody, anti-snake AAV antibody, anti-avian AAV antibody, anti-bovine AAV antibody, anti-canine AAV antibody, anti-equine AAV antibody, anti-ovine AAV antibody, anti-goat AAV antibody, or an anti-shrimp AAV antibody. In some embodiments, the anti-AAV antibody is an anti-AAV type 5 antibody. In some embodiments, the anti-AAV antibody is an anti-AAV type 9 antibody. In some embodiments, the anti-AAV antibody is an anti-AAV type 2 antibody.

In some embodiments, the AAV for the AAV therapy is a different serotype from the AAV that the anti-AAV antibody binds to.

In some embodiments, the ELISA comprises a chemiluminescent ELISA. In some embodiments, the ELISA is a population ELISA.

In some embodiments, the biological sample comprises a serum sample. In some embodiments, the biological sample comprises a blood sample. In some embodiments, the biological sample is diluted prior to the ELISA. In some embodiments, the biological sample is diluted by at least about 1:2, at least about 1:3, at least about 1:4, at least about 1:5, at least about 1:10, at least about 1:20, at least about 1:30, at least about 1:40, at least about 1:50, at least about 1:100, at least about 1:150, at least about 1:200, at least about 1:250, at least about 1:300, at least about 1:350, at least about 1:400, at least about 1:450, at least about 1:500, at least about 1:1000.

In some embodiments, the anti-AAV antibody titer is less than about 800 to less than about 40,000. In some embodiments, the anti-AAV antibody titer is less than about 40,000, less than about 35,000, less than about 30,000, less than about 25,000, less than about 20,000, less than about 15,000, less than about 10,000, less than about 5000, less than about 4000, less than about 3000, less than about 2000, less than about 1000, less than about 900, or less than about 800. In some embodiments, the anti-AAV antibody titer is less than about 800. In some embodiments, the anti-AAV antibody titer is less than about 40,000.

In some embodiments, a subject is identified as having a low titer of the anti-AAV antibody if the biological sample emits less than about 100,000, less than about 10,000, less than about 1000, less than about 950, less than about 900, less than about 850, less than about 800, less than about 750, less than about 700, less than about 650, less than about 600, less than about 550, or less than about 500 chemiluminescence units in a chemiluminescence ELISA. In some embodiments, a subject is identified as having a low titer of the anti-AAV antibody if the biological sample emits less than about 700 chemiluminescence units in a chemiluminescence ELISA. In some embodiments, the low titer of the anti-AAV antibody correlates with a low titer of neutralizing anti-AAV antibodies.

In some embodiments, the AAV therapy comprises administering an AAV comprising a gene of interest. In some embodiments, the gene of interest encodes a biologically active polypeptide. In some embodiments, the AAV further comprises a regulatory sequence. In some embodiments, the regulatory sequence comprises a tissue specific promoter. In some embodiments, the tissue specific promoter drives expression of the gene of interest in a tissue selected from the group consisting of heart, liver, lungs, eyes, nervous system, lymphatic system, muscle and stem cells.

Embodiments

E1. A method of identifying a subject suitable for an adeno associated virus (AAV) therapy, comprising measuring a titer of an antibody or antigen-binding portion thereof that specifically binds to an AAV ("anti-AAV antibody") in a biological sample obtained from the subject using an enzyme-linked immunosorbent assay (ELISA).

E2. The method of E1, further comprising administering an AAV therapy to a subject identified as having a low titer of the anti-AAV antibody.

E3. A method of treating a disease in a subject, comprising administering to the subject an AAV therapy, wherein the subject is identified as having a low titer of an anti-AAV antibody as measured using a biological sample obtained from the subject in an ELISA.

E4. A method of treating a disease in a subject, comprising (1) measuring the titer of an anti-AAV antibody in a biological sample obtained from the subject in an ELISA, wherein the subject is identified as having a low titer of an anti-AAV antibody and (2) administering to the subject identified as having a low titer of an anti-AAV antibody an AAV therapy.

E5. A method of treating a disease in a subject, comprising (1) obtaining a biological sample from the subject, (2) measuring the titer of an anti-AAV antibody in the biological sample in an ELISA, wherein the subject is identified as having a low titer of an anti-AAV antibody, and (3) administering to the subject identified as having a low titer of an anti-AAV antibody an AAV therapy.

E6. The method of any one of E3 to E5, wherein the disease is in the heart, liver, lungs, eyes, blood, nervous system, lymphatic system, muscle, stem cells or any combination thereof.

E7. The method of any one of E3 to E6, wherein the disease is a heart disease.

E8. A high-throughput method of identifying subjects suitable for adeno associated virus (AAV) therapy, comprising measuring a titer of an antibody or antigen-binding portion thereof that specifically binds to an AAV ("anti-AAV antibody") in each of a plurality of biological samples obtained from a corresponding plurality of subjects using an ELISA.

E9. The high-throughput method of E8, wherein the plurality of subjects comprises about 5 to about 10, about 10 to about 20, about 30 to about 40, or about 40 to about 50 subjects.

E10. The high-throughput method of E8 or E9, wherein the titer in each of the plurality of biological samples is measured in parallel or sequentially.

E11. The method of any one of E1 to E10, wherein the titer of an anti-AAV antibody includes a titer of a neutralizing anti-AAV antibody, a titer of a non-neutralizing anti-AAV-antibody, or both.

E12. The method of E11, wherein the ELISA comprises a secondary antibody that binds to the neutralizing anti-AAV antibody or the non-neutralizing anti-AAV-antibody.

E13. The method of E11, wherein the ELISA comprises a secondary antibody that binds to the neutralizing anti-AAV antibody and the non-neutralizing anti-AAV-antibody.

E14. The method of any one of E1 to E13, wherein the AAV therapy comprises administering a recombinant AAV.

E15. The method of any one of E1 to E14, wherein the AAV therapy comprises administering an AAV selected from the group consisting of AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any combination thereof.

E16. The method of any one of E1 to E15, wherein the AAV therapy comprises administering an AAV type 5.

E17. The method of any one of E1 to E16, wherein the AAV therapy comprises administering an AAV type 9.

E18. The method of any one of E1 to E17, wherein the AAV therapy comprises administering an AAV type 2.

E19. The method of any one of E1 to E18, wherein the anti-AAV antibody is an anti-AAV type 1 antibody, anti-AAV type 2 antibody, anti-AAV type 3A antibody, anti-AAV type 3B antibody, anti-AAV type 4 antibody, anti-AAV type 5 antibody, anti-AAV type 6 antibody, anti-AAV type 7 antibody, anti-AAV type 8 antibody, anti-AAV type 9 antibody, anti-AAV type 10 antibody, anti-AAV type 11 antibody, anti-AAV type 12 antibody, anti-AAV type 13 antibody, anti-snake AAV antibody, anti-avian AAV antibody, anti-bovine AAV antibody, anti-canine AAV antibody, anti-equine AAV antibody, anti-ovine AAV antibody, anti-goat AAV antibody, or an anti-shrimp AAV antibody.

E20. The method of any one of E1 to E19, wherein the anti-AAV antibody is an anti-AAV type 5 antibody.

E21. The method of any one of E1 to E19, wherein the anti-AAV antibody is an anti-AAV type 9 antibody.

E22. The method of any one of E1 to E19, wherein the anti-AAV antibody is an anti-AAV type 2 antibody.

E23. The method of any one of E1 to E19, wherein the AAV for the AAV therapy is a different serotype from the AAV that the anti-AAV antibody binds to.

E24. The method of any one of E1 to E23, wherein the ELISA comprises a chemiluminescent ELISA.

E25. The method of any one of E1 to E24, wherein the ELISA is a population ELISA.

E26. The method of any one of E1 to E25, wherein the biological sample comprises a serum sample.

E27. The method of any one of E1 to E26, wherein the biological sample comprises a blood sample.

E28. The method of any one of E1 to E27, wherein the biological sample is diluted prior to the ELISA.

E29. The method of any one of E1 to E28, wherein the biological sample is diluted by at least about 1:2, at least about 1:3, at least about 1:4, at least about 1:5, at least about 1:10, at least about 1:20, at least about 1:30, at least about 1:40, at least about 1:50, at least about 1:100, at least about 1:150, at least about 1:200, at least about 1:250, at least about 1:300, at least about 1:350, at least about 1:400, at least about 1:450, at least about 1:500, at least about 1:1000.

E30. The method of any one of E1 to E29, wherein the anti-AAV antibody titer is less than about 800 to less than about 40,000.

E31. The method of any one of E1 to E30, wherein the anti-AAV antibody titer is less than about 40,000, less than about 35,000, less than about 30,000, less than about 25,000, less than about 20,000, less than about 15,000, less than about 10,000, less than about 5000, less than about 4000, less than about 3000, less than about 2000, less than about 1000, less than about 900, or less than about 800.

E32. The method of any one of E1 to E31, wherein the anti-AAV antibody titer is less than about 800.

E33. The method of any one of E1 to E32, wherein a subject is identified as having a low titer of the anti-AAV antibody if the biological sample emits less than about 100,000, less than about 10,000, less than about 1000, less than about 950, less than about 900, less than about 850, less than about 800, less than about 750, less than about 700, less than about 650, less than about 600, less than about 550, or less than about 500 chemiluminescence units in a chemiluminescence ELISA.

E34. The method of any one of E1 to E33, wherein a subject is identified as having a low titer of the anti-AAV antibody if the biological sample emits less than about 700 chemiluminescence units in a chemiluminescence ELISA.

E35. The method of any one of E2 to E34, wherein the low titer of the anti-AAV antibody correlates with a low titer of neutralizing anti-AAV antibodies.

E36. The method of any one of E1 to E35, wherein the AAV therapy comprises administering an AAV comprising a gene of interest.

E37. The method of E36, wherein the gene of interest encodes a biologically active polypeptide.

E38. The method of E36 or E37, wherein the AAV further comprises a regulatory sequence.

E39. The method of E38, wherein the regulatory sequence comprises a tissue specific promoter.

E40. The method of E38, wherein the tissue specific promoter drives expression of the gene of interest in a tissue selected from the group consisting of heart, liver, lungs, eyes, nervous system, lymphatic system, muscle and stem cells.

BRIEF DESCRIPTION OF THE DRAWINGS

FIGS. 1A-1B are graphical representations of the results of chemiluminescent (FIG. 1A) and colorimetric (FIG. 1B) ELISA detection of anti-rAAV type 9 antibodies in commercially acquired normal human serum samples. Serum samples were diluted as indicated using SBT20 buffer and added to rAAV9S100A1 coated plates. Chemiluminescent (CL) (FIG. 1A) or absorbance (FIG. 1B) units were obtained following the detection of rAAV type 9 bound antibodies with optimized amounts of anti-κ and anti-λ antibodies. Background is the CL (FIG. 1A) or absorbance (FIG. 1B) units observed when control wells incubated with SBT20 buffer are detected with the anti-λ and anti-λ antibodies.

Data was selected in the linear range of serum dilutions for each method to generate the correlative plot shown.

FIGS. 4B-4C show the competition ELISA data at a serum dilution of 1:4 (FIG. 4B) and the monoclonal antibody control (ADK9 at 1:1000; FIG. 4C). Boxed numbers are percent inhibition of signal in the competed serum samples (FIGS. 4B-4C).

DETAILED DESCRIPTION OF THE DISCLOSURE

Figure 2:
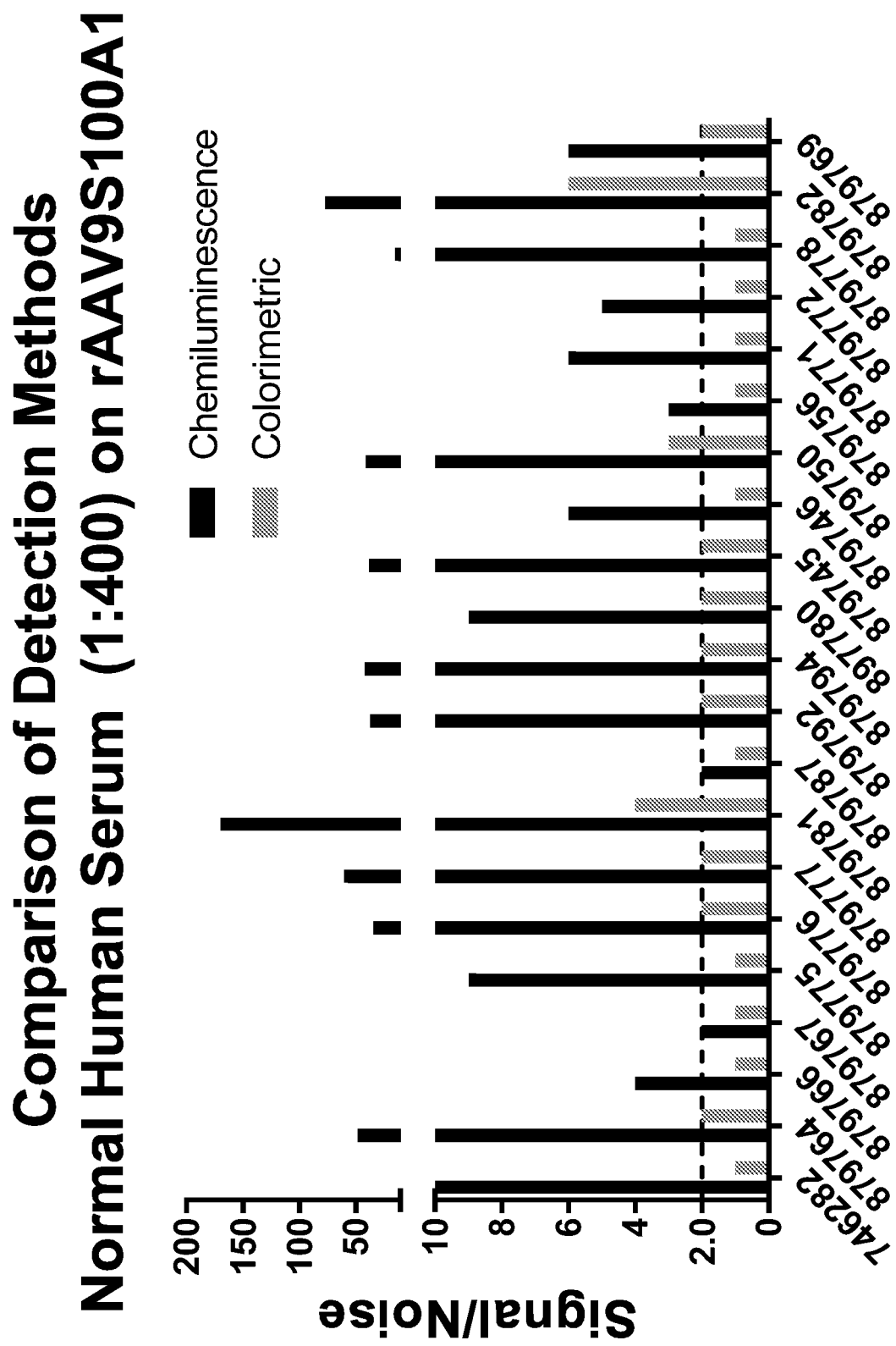
FIG. 2 is a bar graph, representing a comparison of signal-to-noise ratios for chemiluminescence (black bars) and colorimetric (grey bars) ELISA detection methods. Chemiluminescence or absorbance units at a 400-fold serum dilution were obtained using anti-κ and anti-λ detection antibodies and divided by data units obtained with only SBT20 buffer incubation and anti-κ and anti-λ detection antibodies on rAAV9 coated plates.

Certain aspects of the present disclosure are directed to methods of identifying a subject suitable for an adeno associated virus (AAV) therapy, comprising measuring a titer of an antibody or antigen-binding portion thereof that binds to an AAV ("anti-AAV antibody") in a biological sample obtained from the subject using an enzyme-linked immunosorbent assay (ELISA). Some aspects of the present disclosure are directed to methods of treating a disease in a subject, comprising administering to the subject an AAV therapy. In certain aspects, the subject is identified as having a low titer of an anti-AAV antibody as measured using a biological sample obtained from the subject in an ELISA. In some aspects, the present disclosure is directed to a high-throughput method of identifying subjects suitable for an AAV therapy, comprising measuring a titer of an anti-AAV antibody in each of a plurality of biological samples obtained from a corresponding plurality of subjects using an ELISA.

I. Terms

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which is to be understood by reference to the specification as a whole. The terms defined immediately below are to be understood by reference to the specification in its entirety.

As used herein, the term "adeno-associated virus" or "AAV" includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, those AAV serotypes and clades disclosed by Gao et al. (J. Virol. 78:6381 (2004)) and Moris et al. (Virol. 33:375 (2004)), and any other AAV now known or later discovered. See, e.g., FIELDS et al. VIROLOGY, volume 2, chapter 69 (4th ed., Lippincott-Raven Publishers). AAV refers to a *Dependoparvovirus* (genus) within the Parvoviridae family of viruses. For example, the AAV can be an AAV derived from a naturally occurring "wild-type" virus, an AAV derived from a recombinant AAV (rAAV) genome packaged into a capsid derived from capsid proteins encoded by a naturally occurring cap gene and/or a rAAV genome packaged into a capsid derived from capsid proteins encoded by a non-natural capsid cap gene. As used herein, "AAV" may be used to refer to the virus itself or derivatives thereof. The term covers all subtypes and both naturally occurring and recombinant forms, except where specifically indicated otherwise. AAV includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc. See, e.g., BERNARD N. FIELDS et al., VIROLOGY, volume 2, chapter 69 (3 d ed., Lippincott-Raven Publishers).

The term "rAAV" refers to a "recombinant AAV." In some embodiments, a recombinant AAV has an AAV genome in which part or all of the rep and cap genes have been replaced with heterologous sequences. An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

A "capsid-free" or "capsid-less" (or variations thereof) vector or nucleic acid molecule refers to a vector construct free from a capsid. In some embodiments, the capsid-less vector or nucleic acid molecule does not contain sequences encoding, e.g., an AAV Rep protein.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the virus or particle comprises a heterologous polynucleotide (i.e. a polynucleotide other than a wild-type AAV genome such as a transgene to be delivered to a mammalian cell), it may be referred to as an "rAAV vector particle." Thus, production of an rAAV particle necessarily includes the production of an rAAV vector, as such a vector is contained within an rAAV particle.

A "helper virus" for AAV refers to a virus that allows AAV (e.g., wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

As used herein, an "inverted terminal repeat" (or "ITR") refers to a nucleic acid subsequence located at either the 5' or 3' end of a single stranded nucleic acid sequence, which comprises a set of nucleotides (initial sequence) followed downstream by its reverse complement, i.e., palindromic sequence. The intervening sequence of nucleotides between the initial sequence and the reverse complement can be any length.

The term "tropism" as used herein refers to the ability of an AAV vector or virion to infect one or more specified cell types, but can also encompass how the vector functions to transduce the cell in the one or more specified cell types; i.e., tropism refers to preferential entry of the AAV vector or virion into certain cell or tissue type(s) and/or preferential interaction with the cell surface that facilitates entry into certain cell or tissue types, optionally and preferably followed by expression (e.g., transcription and, optionally, translation) of sequences carried by the AAV vector or virion in the cell, e.g., for a recombinant virus, expression of the heterologous nucleotide sequence(s). As used herein, the term "transduction" refers to the ability of an AAV vector or virion to infect one or more particular cell types; i.e., transduction refers to entry of the AAV vector or virion into the cell and the transfer of genetic material contained within the AAV vector or virion into the cell to obtain expression from the vector genome. In some cases, but not all cases, transduction and tropism may correlate.

"Administering" refers to the physical introduction of a therapeutic agent to a subject, using any of the various methods and delivery systems known to those skilled in the art. Exemplary routes of administration, e.g., for an AAV therapy, include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, an immunoglobulin which binds specifically to an antigen and comprises at least two heavy (H) chains and two light (L) chains interconnected by disulfide bonds. Each H chain comprises a heavy chain variable region (abbreviated herein as $V_H$) and a heavy chain constant region. The heavy chain constant region comprises at least three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antibody" (Ab) also includes, without limitation, any antigen-binding portion of an immunoglobulin which binds specifically to an antigen and is as defined herein.

An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1, respectively) that is encoded by the heavy chain constant region genes. The term "antibody" includes, by way of example, both naturally occurring and non-naturally occurring antibodies; monoclonal and polyclonal antibodies; chimeric and humanized antibodies; human or non-human antibodies; wholly synthetic antibodies; and single chain antibodies. A non-human antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to an AAV is substantially free of antibodies that bind specifically to antigens other than the AAV). Moreover, an isolated antibody can be substantially free of other cellular material and/or chemicals.

The term "monoclonal antibody" (mAb) refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies can be produced by hybridoma, recombinant, transgenic, or other techniques known to those skilled in the art.

The term "neutralizing antibody" (nAb) refers to an antibody that binds to a target and inhibits or blocks the function of the target. For example, a neutralizing antibody that binds an AAV-9 is capable of binding AAV-9 and disrupting the function of the AAV-9. In some embodiments, a neutralizing AAV antibody binds an AAV viral particle before the viral particle binds and enters a target cell, preventing the viral particle from binding and/or entering the target cell and releasing a transgene within the cell.

An "anti-antigen antibody" refers to an antibody that binds specifically to the antigen. For example, an anti-AAV antibody binds specifically to an AAV viral particle.

An "antigen-binding portion" of an antibody (also called an "antigen-binding fragment") refers to one or more fragments of an antibody that retain the ability to bind specifically to the antigen bound by the whole antibody.

A "high-throughput method," as used herein, refers to a method or assay that allows for the characterization of a plurality of biological samples in a single assay. For example a high-throughput method can be used to measure the antibody titers in at least 5, at least 10, at least 15, at least 20, at least 25, at least 30, at least 35, at least 40, at least 45, at least 50, at least 60, at least 70, at least 80, at least 90, or at least 100 biological samples in a single assay. In some embodiments, a high-throughput method or assay uses a multi-well plate. In some embodiments, the plurality of biological samples are measured in parallel. As used herein, samples that are measured in "parallel" are measured concurrently. In some embodiments, the plurality of biological samples are measured sequentially.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease.

A "subject" includes any human or non-human animal. The term "nonhuman animal" includes, but is not limited to, vertebrates such as nonhuman primates, sheep, dogs, and rodents such as mice, rats, and guinea pigs. In some embodiments, the subject is a human. The terms "subject" and "patient" are used interchangeably herein.

A "titer" or an "antibody titer," as used herein, refers to the amount of a particular antibody in a sample, e.g., in a biological sample obtained from a subject. The titer of an antibody can be measured using any methods known in the art. In some embodiments, the titer of an antibody is measured by serially diluting a sample containing the antibody until the antibody is no longer detected over background. In such an example, the titer of an antibody is expressed as the fold dilution below which the concentration of the antibody is reduced to background levels. For example, if a dilution of 1:800 is the highest dilution in a series of dilutions to be detected above background levels, then the titer of the antibody is expressed as 800. If a dilution of 1:40,000 is the highest dilution in a series of dilutions to be detected above background levels, then the titer of the antibody is expressed as 40,000. In some embodiments, the titer of the anti-AAV antibody is less than about 40,000. In certain embodiments, the titer of the anti-AAV antibody is less than about 800.

In some embodiments, the antibody titer is measured using an enzyme-linked immunosorbent assay (ELISA). Any ELISA known in the art can be used in the methods of the present disclosure. ELISA is characterized by a series of antibody interactions to detect the presence of a target in a sample in vitro. ELISAs can include a direct assay, an indirect assay, or a capture assay (i.e., a sandwich assay). In a direct assay, an antigen is bound to a surface. A primary antibody conjugated to an enzyme is applied to the surface, and the primary antibody binds the antigen. A substrate is then added that is acted on by the enzyme, producing a detectable signal, which indicates the presence of the antigen on the surface. In an indirect assay, an antigen is bound to a surface. A primary antibody is then applied to the surface, and the primary antibody binds the antigen. A secondary antibody conjugated to an enzyme is then applied to the surface. The secondary antibody is capable of binding the primary antibody. A substrate is then added that is acted on by the enzyme, producing a detectable signal, which indicates the presence of the antigen on the surface. In a capture assay, an antibody is bound to the surface, and a sample comprising the antigen is applied to the surface. A primary antibody and a secondary antibody are then applied as in the indirect assay.

In some embodiments, the ELISA is a "chemiluminescent ELISA." A "chemiluminescent ELISA" or a "luminescent assay" or a "chemiluminescent assay" is a type of ELISA that uses the emission of light as an indicator of the presence of a target. The intensity of the emitted light can then be measured and correlated with the abundance of the target in a sample. In a chemiluminescent ELISA, an enzyme converts a substrate to a reaction product that emits photons of light. Luminescence is described as the emission of light from a substance as it returns from an electronically excited state to a ground state. Chemiluminescence is light produced by a chemical reaction. When the excited intermediates return back to their stable ground state, a photon is released, which is detected by a sensor in a luminescent signal instrument. The intensity of the luminescent signal can be expressed in chemiluminescence units, wherein the greater the number of detected chemiluminescence units is, the higher the titer of the target in the biological sample.

Any chemiluminescent enzyme and substrate can be used in the methods disclosed herein. In some embodiments, the chemiluminescent enzyme comprises alkaline phosphatase (AP). In some embodiments, the chemiluminescent enzyme comprises horse radish peroxidase (HRP). In some embodiments, the chemiluminescent enzyme comprises beta galactosidase and beta lactamase.

In some embodiments, the ELISA assay comprises (1) coating a surface with an AAV target, e.g., AAV-9 viral particles; (2) contacting the surface with a sample that comprises one or more anti-AAV antibodies, e.g., a biological sample obtained from a subject; (3) contacting the surface with a second antibody fused to an enzyme, e.g., horse radish peroxidase (HRP), wherein the second antibody is capable of binding the anti-AAV antibody; (4) contacting the surface with a chemiluminescent substrate; and (5) measuring the light emitted from the surface.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks, and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. Methods of the Disclosure

Certain aspects of the present disclosure are directed to methods of identifying a subject suitable for an adeno associated virus (AAV) therapy, comprising measuring a titer of an antibody or antigen-binding portion thereof that specifically binds to an AAV ("anti-AAV antibody") in a biological sample obtained from the subject using an ELISA. In some embodiments, the method further comprises administering an AAV therapy to a subject identified as having a low titer of the anti-AAV antibody.

Some aspects of the present disclosure are directed to methods of treating a disease in a subject, comprising administering to the subject an AAV therapy, wherein the subject is identified as having a low titer of an anti-AAV antibody as measured using a biological sample obtained from the subject in an ELISA. Some aspects of the present disclosure are directed to methods of treating a disease in a subject, comprising (1) measuring the titer of an anti-AAV antibody in a biological sample obtained from the subject in an ELISA, and (2) administering to the subject an AAV therapy, wherein the subject is identified as having a low titer of an anti-AAV antibody. In some aspects, the disclosure is directed to a method of treating a disease in a subject, comprising (1) obtaining a biological sample from the subject, (2) measuring the titer of an anti-AAV antibody in the biological sample in an ELISA, and (3) administering to the subject an AAV therapy, wherein the subject is identified as having a low titer of an anti-AAV antibody. In some aspects, the disclosure is directed to a method of treating a disease in a subject, comprising (1) obtaining or having obtained a biological sample from the subject, (2) measuring or having measured the titer of an anti-AAV antibody in the biological sample in an ELISA, and (3) administering to the subject an AAV therapy, wherein the subject is identified as having a low titer of an anti-AAV antibody.

The methods of the present disclosure are useful for the treatment of any disease or condition known in the art that can be treated using an AAV therapy. For example, the methods disclosed herein can be used in the treatment of a disease or condition that affects a subject's heart, liver, lungs, eyes, blood, nervous system, lymphatic system, muscle, stem cells, and any combination thereof. In some embodiments, the disease or condition is a disease or condition affecting the central nervous system. In some embodiments, the disease or condition comprises a heart disease. In certain embodiments, the disease or condition comprises heart failure. In certain embodiments, the disease or condition comprises acute or chronic heart failure. In particular embodiments, the disease or condition comprises heart failure with reduced ejection fraction (HFrEF). In particular embodiments, the disease or condition comprises heart failure with preserved ejection fraction. In some embodiments, the disease or condition is cystic fibrosis, hemophilia B, arthritis, hereditary emphysema, leber's congenital amaurosis, macular degeneration (e.g., age-related macular degeneration), Duchenne muscular dystrophy (DMD), Parkinson's disease, Canavan disease, Batten disease, Alzheimer's disease, spinal muscular atrophy, congestive heart failure, biallelic RPE65 mutation-associated retinal dystrophy, or any combination thereof.

Some aspects of the present disclosure are directed to a high-throughput method of identifying subjects suitable for an AAV therapy, comprising measuring a titer of an anti-AAV antibody in each of a plurality of biological samples obtained from a corresponding plurality of subjects using an ELISA. In some embodiments, the plurality of subjects comprises at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 150, at least about 200, at least about 250, at least about 500, at least about 750, or at least about 1000 subjects. In some embodiments, the plurality of subjects comprises at least about 10 subjects. In some embodiments, the plurality of subjects comprises at least about 20 subjects. In some embodiments, the plurality of subjects comprises at least about 30 subjects. In some embodiments, the plurality of subjects comprises at least about 40 subjects. In some embodiments, the plurality of subjects comprises at least about 50 subjects. In some embodiments, the plurality of subjects comprises at least about 60 subjects. In some embodiments, the plurality of subjects comprises at least about 70 subjects. In some embodiments, the plurality of subjects comprises at least about 80 subjects. In some embodiments, the plurality of subjects comprises at least about 90 subjects. In some embodiments, the plurality of subjects comprises at least about 100 subjects.

In some embodiments, the plurality of subjects comprises 2 to about 100 subjects.

In some embodiments, the plurality of subjects comprises 2 to about 90 subjects, 2 to about 85 subjects, 2 to about 80 subjects, 2 to about 75 subjects, 2 to about 70 subjects, 2 to about 65 subjects, 2 to about 60 subjects, 2 to about 55 subjects, 2 to about 50 subjects, 2 to about 45 subjects, 2 to about 40 subjects, 2 to about 35 subjects, 2 to about 30 subjects, 2 to about 25 subjects, 2 to about 20 subjects, 2 to about 15 subjects, 2 to about 10 subjects, or 2 to about 5 subjects.

In some embodiments, the plurality of subjects comprises about 5 to about 100 subjects, about 10 to about 100 subjects, about 15 to about 100 subjects, about 20 to about 100 subjects, about 25 to about 100 subjects, about 30 to about 100 subjects, about 35 to about 100 subjects, about 40 to about 100 subjects, about 45 to about 100 subjects, about 50 to about 100 subjects, about 55 to about 100 subjects, about 60 to about 100 subjects, about 65 to about 100 subjects, about 70 to about 100 subjects, about 75 to about 100 subjects, about 80 to about 100 subjects, about 85 to about 100 subjects, about 90 to about 100 subjects, or about 95 to about 100 subjects.

In some embodiments, the plurality of subjects comprises about 10 to about 90 subjects, about 20 to about 80 subjects, about 30 to about 70 subjects, about 40 to about 60 subjects, about 25 to about 50 subjects, about 50 to about 75 subjects, about 25 to about 75 subject, or about 50 to about 100 subjects. In some embodiments, the plurality of subjects comprises about 5 to about 10, about 10 to about 20, about 30 to about 40, or about 40 to about 50 subjects.

In some embodiments, the titer in each of the plurality of biological samples is measured in parallel. In some embodiments, the titer in each of the plurality of biological samples is measured sequentially.

In some embodiments, the methods of the present disclosure comprise measuring the titer of an anti-AAV antibody in a biological sample or in each of a plurality of biological samples. The anti-AAV antibody can include a single class of an anti-AAV antibody, e.g., only neutralizing anti-AAV antibodies, or a mix of more than one class of anti-AAV antibodies, e.g., neutralizing and non-neutralizing anti-AAV antibodies. In some embodiments, the titer of the anti-AAV antibody includes a titer of a neutralizing anti-AAV antibody, a titer of a non-neutralizing anti-AAV antibody, or both. In certain embodiments, the titer of the anti-AAV antibody includes only the titer of a neutralizing anti-AAV antibody or the titer of a non-neutralizing antibody. In certain embodiments, the ELISA comprises a secondary antibody that binds to the neutralizing anti-AAV antibody or the non-neutralizing anti-AAV-antibody. In some embodiments, the methods of the present disclosure detect both neutralizing and non-neutralizing anti-AAV antibodies. In certain embodiments, the ELISA comprises a secondary antibody that binds to the neutralizing anti-AAV antibody and the non-neutralizing anti-AAV-antibody. As described herein, the present disclosure surprisingly identifies a correlation between the total anti-AAV antibody titer and the titer of neutralizing anti-AAV antibodies in a biological sample.

The anti-AAV antibody can be any single type or class of anti-AAV antibody, e.g., an anti-AAV-9 antibody or an anti-AAV-2 antibody or an AAV-5 antibody, or a mix of more than one anti-AAV antibody, e.g., an anti-AAV-9 antibody and an anti-AAV-2 antibody; an anti-AAV-9 antibody and an anti-AAV-5; an anti-AAV-2 antibody and an anti-AAV-5. The anti-AAV antibody can also be any isotype, e.g., IgG, IgM, IgD, IgA or IgE, or combinations thereof.

II.A. Adeno-Associate Virus (AAV)

Certain aspects of the present disclosure are directed to methods of detecting anti-AAV antibodies and/or administering an AAV to a subject. Adeno-associated virus (AAV) is a nonenveloped, single-stranded DNA virus of the Parvoviridae family. In contrast to most other members of the Parvoviridae family, AAV is replication defective and is only able to replicate efficiently in the presence of a helper virus such as adenovirus or herpes virus.

AAV was first reported in the mid 1960's as a contaminant of viral preparations of adenovirus. See Atchison R W, Casto B C, HAMMON W M. *Science.* 149(3685), 754-756 (1965). Since then, progressively safer and more effective methods to use AAV as a recombinant DNA vector have been developed. See, e.g., Hermonat P. L. and Muzyczka N. *Proc Natl Acad Sci USA.* 81(20), 6466-6470 (1984). 3. Laughlin C. A., et al. *Gene,* 23(1), 65-73 (1983). Matsushita T., et al. *Gene Ther.* 5(7), 938-945 (1998). Xiao X., et al. *Journal of Virology.* 72(3), 2224-2232 (1998). It has been reported that low numbers of AAV genomes can integrate into the host chromosome, (Cheung A K, Hoggan M D, Hauswirth W W, et al. Integration of the adeno-associated virus genome into cellular DNA in latently infected human detroit 6 cells. J Virol 1980; 33:739-748). AAV is immunologically distinct from any known adenovirus antigen. The AAV capsid contains a single-stranded DNA (ssDNA) genome (Rose J A, Berns K I, Hoggan M D, et al. Proc Natl Acad Sci USA 1969; 64:863-869.

AAV has a single stranded, 4.7 kb DNA genome encoding a replication (rep) gene and a capsid (cap) genes flanked by two inverted terminal repeats (ITRs). It is predominantly non-integrating and forms stable episomes in non-dividing tissue. In spite of its high sero-prevalence in the adult human population, it has not been associated with any human disease. See Gonsalves, M. *Virol. J.* 2, 43 (2005). AAV's stable expression in tissues, its lack of pathogenicity, and its ease of high titer production have made it a very attractive and popular gene transfer platform.

A recombinant AAV is a genetically manipulated AAV in which part or all of the rep and cap genes have been replaced with heterologous sequences. Just as wild-type AAV, rAAV can trigger long-term transgene expression in postmitotic tissues, most likely because the rAAV's recombinant genome persists as largely circular episomes within the nucleus. rAAVs only cis-element required for the production of rAAVs is the AAV inverted terminal repeats (ITRs), whereas rep, cap, and adenoviral helper genes can be provided in trans. Thus, in some embodiments disclosed herein, rAAVs contain only the transgene DNA flanked by the ITRs, and this genome is encapsidated within a serotype-specific capsid.

AAV possesses unique features that make it attractive as a vector for delivering foreign DNA to cells. AAV infection of cells in culture has generally been noncytopathic, and natural infection of humans and other animals is silent and asymptomatic. Moreover, AAV infects many different types of mammalian cells allowing the possibility of targeting many different tissues in vivo. AAV also possess additional advantages that make it a particularly attractive viral system for gene delivery, including promotion of a milder immune response compared to other forms of gene delivery and persistent expression in both dividing and quiescent cells as a non-integrating vector. Also, AAV withstands the conditions used to inactivate adenovirus (56° to 65° C. for several hours), making cold preservation of rAAV-based vaccines less critical.

Helper virus is not required for AAV transduction and entry of the AAV genome into the target cell. Furthermore, because the signals directing AAV replication, genome encapsidation and integration are contained within the ITRs of the AAV genome, the internal approximately 4.7 kb of the genome (encoding replication and structural capsid proteins, rep-cap) may thus be replaced with foreign DNA such as a gene cassette containing a promoter, a DNA of interest and a polyadenylation signal, without loss of any functionality critical for AAV use as gene-therapeutic agent.

AAV vectors can include additional elements that function in cis or in trans. In particular embodiments, an AAV vector that includes a vector genome also has one or more inverted terminal repeat (ITR) sequences that flank the 5' or 3' terminus of the donor sequence; an expression control element that drives transcription (e.g., a promoter or enhancer) of the donor sequence, such as a constitutive or regulatable control element, or tissue-specific expression control element; an intron sequence, a stuffer or filler polynucleotide sequence; and/or a poly-Adenine sequence located 3' of the donor sequence.

In some embodiments, AAV replicates using a helper virus. A variety of such helper viruses for AAV are known in the art, including adenoviruses, herpesviruses and poxviruses such as vaccinia. Individual adenovirus types encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

Exemplary AAV vectors include capsid proteins of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Recombinant AAV vectors of the invention also include capsid proteins from any of AAV1, AAV2, AAV3, AAV4, AAV5, AAV6, AAV7, AAV8, AAV9, AAV10, AAV11, Rh10, Rh74 or AAV-2i8, and variants thereof. Particular capsid variants include capsid variants of AAV1, AAV2, AAV3, AAV4, AAV5, AAV6, AAV7, AAV8, AAV9, AAV10, AAV11, Rh10, Rh74 or AAV-2i8, such as a capsid protein with an amino acid substitution, deletion or insertion/addition.

Certain aspects of the present disclosure are directed to methods of detecting anti-AAV antibodies in a biological sample. The anti-AAV antibodies can be specific for any AAV known in the art or any aspect, e.g., surface protein, of any AAV known in the art. Exemplary AAV include but are not limited to AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, and shrimp AAV. In certain embodiments, the anti-AAV antibody binds anti-AAV type 1. In some embodiments, the anti-AAV antibody is an anti-AAV type 1 antibody, anti-AAV type 2 antibody, anti-AAV type 3A antibody, anti-AAV type 3B antibody, anti-AAV type 4 antibody, anti-AAV type 5 antibody, anti-AAV type 6 antibody, anti-AAV type 7 antibody, anti-AAV type 8 antibody, anti-AAV type 9 antibody, anti-AAV type 10 antibody, anti-AAV type 11 antibody, anti-AAV type 12 antibody, anti-AAV type 13 antibody, anti-snake AAV antibody, anti-avian AAV antibody, anti-bovine AAV antibody, anti-canine AAV antibody, anti-equine AAV antibody, anti-ovine AAV antibody, anti-goat AAV antibody, or an anti-shrimp AAV antibody. In certain embodiments, the anti-AAV antibody binds anti-AAV type 2. In certain embodiments, the anti-AAV antibody binds anti-AAV type 3. In certain embodiments, the anti-AAV antibody binds anti-AAV type 4. In certain embodiments, the anti-AAV antibody binds anti-AAV type 5. In certain embodiments, the anti-AAV antibody binds anti- AAV type 6. In certain embodiments, the anti-AAV antibody binds anti-AAV type 7. In certain embodiments, the anti-AAV antibody binds anti-AAV type 8. In certain embodiments, the anti-AAV antibody binds anti-AAV type 9. In certain embodiments, the anti-AAV antibody binds anti-AAV type 10. In certain embodiments, the anti-AAV antibody binds anti-AAV type 11. In certain embodiments, the anti-AAV antibody binds anti-AAV type 12. In certain embodiments, the anti-AAV antibody binds anti-AAV type 13.

In some embodiments, the anti-AAV antibody binds more than one AAV serotype, e.g., AAV type 2 and AAV type 9. In some embodiments, the anti-AAV antibody binds one AAV serotype, e.g., AAV type 9 or AAV type 2, with a higher affinity than any other AAV serotype. In certain embodiments, the anti-AAV antibody only specifically binds one AAV serotype, e.g., AAV type 9 or AAV type 2.

In certain aspects of the disclosure, the method further comprises administering an AAV therapy to the subject. In some embodiments, the AAV therapy comprises administering a recombinant AAV. Any recombinant AAV known in the art and/or disclosed herein can be used in the methods of the present disclosure. In some embodiments, the AAV therapy comprises administering an AAV selected from the group consisting of AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any combination thereof. In certain embodiments, the AAV therapy comprises administering an AAV type 1. In certain embodiments, the AAV therapy comprises administering an AAV type 2. In certain embodiments, the AAV therapy comprises administering an AAV type 3. In certain embodiments, the AAV therapy comprises administering an AAV type 4. In certain embodiments, the AAV therapy comprises administering an AAV type 5. In certain embodiments, the AAV therapy comprises administering an AAV type 6. In certain embodiments, the AAV therapy comprises administering an AAV type 7. In certain embodiments, the AAV therapy comprises administering an AAV type 8. In certain embodiments, the AAV therapy comprises administering an AAV type 9. In certain embodiments, the AAV therapy comprises administering an AAV type 10. In certain embodiments, the AAV therapy comprises administering an AAV type 11. In certain embodiments, the AAV therapy comprises administering an AAV type 12. In certain embodiments, the AAV therapy comprises administering an AAV type 13.

In some aspects the disclosure relates to AAVs having distinct tissue targeting capabilities (e.g., tissue tropisms). In some embodiments, the variant AAV capsid polypeptides further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow, progenitor cells, induced pluripotent stem cells, and reprogrammed stem cells. In some embodiments, adult stem cells can include organoid stem cells (i.e., stem cells derived from any organ or organ system of interest within the body). In some embodiments, the target tissue of an AAV is gonad, diaphragm, heart, stomach, liver, spleen, pancreas, or kidney. In some embodiments, the AAV targets organs of the body include, but are not limited to, skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the AAV for the AAV therapy is a different serotype from the AAV that the anti-AAV antibody binds to. For example, in some embodiments, the AAV therapy comprises administration of an AAV type 2 and the anti-AAV antibody is an anti-AAV type 9 antibody. In some embodiments, the AAV for the AAV therapy is the same serotype as the AAV that the anti-AAV antibody binds to. In certain embodiments, the AAV therapy comprises administering a recombinant AAV type 9, and the anti-AAV antibody is an anti-AAV type 9 antibody. In certain embodiments, the AAV therapy comprises administering a recombinant AAV type 5, and the anti-AAV antibody is an anti-AAV type 5 antibody. In certain embodiments, the AAV therapy comprises administering a recombinant AAV type 2, and the anti-AAV antibody is an anti-AAV type 2 antibody.

II.A.1. Replication, Capsid, and Assembly AAV Genes

The single-stranded genome of AAV comprises three genes, rep (Replication), cap (Capsid), and aap (Assembly). These three genes give rise to at least nine gene products through the use of three promoters, alternative translation start sites, and differential splicing.

The rep gene encodes four proteins (Rep78, Rep68, Rep52, and Rep40), which are required for viral genome replication and packaging.

Cap gene expression gives rise to the viral capsid proteins (VP1; VP2; VP3), which form the outer capsid shell that protects the viral genome, as well as being actively involved in cell binding and internalization. It is estimated that the viral coat is comprised of 60 proteins arranged into an icosahedral structure.

The aap gene encodes the assembly-activating protein (AAP) in an alternate reading frame overlapping the cap gene. This nuclear protein is thought to provide a scaffolding function for capsid assembly and plays a role in nucleolar localization of VP proteins in some AAV serotypes.

In some embodiments, one or more of the rep, cap, or aap genes are naturally occurring, e.g. the rep, cap, or app genes comprise all or a portion of parvovirus rep, cap, or aap genes. In some embodiments, the one or more of the rep, cap, or aap genes comprise a synthetic sequence.

In one embodiment, the rep gene comprises a synthetic sequence. In one embodiment, the cap gene comprises a synthetic sequence. In one embodiment, the aap gene comprises a synthetic sequence. In one embodiment, the rep and cap genes comprise a synthetic sequence. In one embodiment, the rep and aap genes comprise a synthetic sequence. In one embodiment, the cap and aap genes comprise a synthetic sequence. In one embodiment, the rep, cap, and aap genes comprise a synthetic sequence.

In some embodiments, rep is from an AAV genome selected from AAV1, AAV2, AAV3, AAV4, AAV5, AAV6, AAV7, AAV8, AAV9, AAV10 AAV11, and any combination thereof. In a particular embodiment, rep is from the AAV1 genome. In a particular embodiment, rep is from the AAV2 genome. In a particular embodiment, rep is from the AAV3 genome. In a particular embodiment, rep is from the AAV4 genome. In a particular embodiment, rep is from the AAV5 genome. In a particular embodiment, rep is from the AAV6 genome. In a particular embodiment, rep is from the AAV7 genome. In a particular embodiment, rep is from the AAV8 genome. In a particular embodiment, rep is from the AAV9 genome. In a particular embodiment, rep is from the AAV10 genome. In a particular embodiment, rep is from the AAV11 genome.

In some embodiments, cap is from an AAV genome selected from AAV1, AAV2, AAV3, AAV4, AAV5, AAV6, AAV7, AAV8, AAV9, AAV10 AAV11, and any combination thereof. In a particular embodiment, cap is from the AAV1 genome. In a particular embodiment, cap is from the AAV2 genome. In a particular embodiment, cap is from the AAV3 genome. In a particular embodiment, cap is from the AAV4 genome. In a particular embodiment, cap is from the AAV5 genome. In a particular embodiment, cap is from the AAV6 genome. In a particular embodiment, cap is from the AAV7 genome. In a particular embodiment, cap is from the AAV8 genome. In a particular embodiment, cap is from the AAV9 genome. In a particular embodiment, cap is from the AAV10 genome. In a particular embodiment, cap is from the AAV11 genome.

In some embodiments, aap is from an AAV genome selected from AAV1, AAV2, AAV3, AAV4, AAV5, AAV6, AAV7, AAV8, AAV9, AAV10 AAV11, and any combination thereof. In a particular embodiment, aap is from the AAV1 genome. In a particular embodiment, aap is from the AAV2 genome. In a particular embodiment, aap is from the AAV3 genome. In a particular embodiment, aap is from the AAV4 genome. In a particular embodiment, aap is from the AAV5 genome. In a particular embodiment, aap is from the AAV6 genome. In a particular embodiment, aap is from the AAV7 genome. In a particular embodiment, aap is from the AAV8 genome. In a particular embodiment, aap is from the AAV9 genome. In a particular embodiment, aap is from the AAV10 genome. In a particular embodiment, aap is from the AAV11 genome.

It is to be understood that a particular AAV genome described herein could have genes from different AAV genomes (e.g., genomes from AAV1, AAV2, AAV3, AAV4, AAV5, AAV6, AAV7, AAV8, AAV9, AAV10, and AAV11). Thus, disclosed herein are AAVs that comprise any possible permutation of rep, cap, or aap.

In some embodiments disclosed herein, the AAV is recombinant AAV (rAAV). In some embodiments, the rAAV lacks one or more of the rep gene, the cap gene, and the aap gene. In some embodiments, the rAAV lacks a rep gene. In some embodiments, the rAAV lacks a cap gene. In some embodiments, the rAAV lacks an aap gene. In some embodiments, the rAAV lacks a rep gene and lacks a cap gene. In some embodiments, the rAAV lacks a rep gene and lacks an aap gene. In some embodiments, the rAAV lacks a cap gene and lacks an aap gene. In some embodiments, the rAAV lacks a rep gene, a cap gene, and an aap gene.

In some embodiments disclosed herein, the rAAV is modified so that one or more of the rep gene, the cap gene, and the aap gene is mutated so that expression of one or more of the AAV genes is modified. In some embodiments, the rep gene is mutated. In some embodiments, the cap gene is mutated. In some embodiments, the aap gene is mutated. In some embodiments, the rep gene and the cap gene are mutated. In some embodiments, the rep gene and the aap gene are mutated. In some embodiments, the cap gene and the aap gene are mutated. In some embodiments, the cap gene, the rep gene, and the aap gene are mutated.

II.A.2. Inverted Terminal Repeats

In certain embodiments, the AAV comprises a first ITR, e.g., a 5' ITR, and second ITR, e.g., a 3' ITR. Typically, ITRs are involved in parvovirus (e.g., AAV) DNA replication and rescue, or excision, from prokaryotic plasmids (Samulski et al., 1983, 1987; Senapathy et al., 1984; Gottlieb and Muzyczka, 1988). In addition, ITRs are reported to be the minimum sequences required for AAV proviral integration and for packaging of AAV DNA into virions (McLaughlin et al., 1988; Samulski et al., 1989). These elements are essential for efficient multiplication of a parvovirus genome.

In some embodiments, the ITR comprises a naturally occurring ITR, e.g., the ITR comprises all or a portion of a parvovirus ITR. In some embodiments, the ITR comprises a synthetic sequence. In one embodiment, the first ITR or the second ITR comprises a synthetic sequence. In another embodiment, each of the first ITR and the second ITR comprises a synthetic sequence. In some embodiments, the first ITR or the second ITR comprises a naturally occurring sequence. In another embodiment, each of the first ITR and the second ITR comprises a naturally occurring sequence.

In some embodiments, the ITR comprises an ITR from an AAV genome. In some embodiments, the ITR is an ITR of an AAV genome selected from AAV1, AAV2, AAV3, AAV4, AAV5, AAV6, AAV7, AAV8, AAV9, AAV10 AAV11, and any combination thereof. In a particular embodiment, the ITR is an ITR of the AAV2 genome. In another embodiment, the ITR is a synthetic sequence genetically engineered to include at its 5' and 3' ends ITRs derived from one or more of AAV genomes. In some embodiments, the ITRs are derived from the same genome, e.g., from the genome of the same virus, or from different genomes, e.g., from the genomes of two or more different AAV genomes. In certain embodiments, the ITRs are derived from the same AAV genome. In a specific embodiment, the two ITRs present in the nucleic acid molecule of the invention are the same, and can in particular be AAV2 ITRs, AAV5 ITRs or AAV9 ITRs. In one particular embodiment, the first ITR and the second ITR are identical.

In some embodiments, the ITRs form hairpin loop structures. In one embodiment, the first ITR forms a hairpin structure. In another embodiment, the second ITR forms a hairpin structure. Still in another embodiment, both the first ITR and the second ITR form hairpin structures.

In some embodiments, an ITR in a nucleic acid molecule described herein is a transcriptionally activated ITR. A transcriptionally-activated ITR can comprise all or a portion of a wild-type ITR that has been transcriptionally activated by inclusion of at least one transcriptionally active element. Various types of transcriptionally active elements are suitable for use in this context. In some embodiments, the transcriptionally active element is a constitutive transcriptionally active element. Constitutive transcriptionally active elements provide an ongoing level of gene transcription, and are preferred when it is desired that the transgene be expressed on an ongoing basis. In other embodiments, the transcriptionally active element is an inducible transcriptionally active element. Inducible transcriptionally active elements generally exhibit low activity in the absence of an inducer (or inducing condition), and are up-regulated in the presence of the inducer (or switch to an inducing condition). Inducible transcriptionally active elements may be preferred when expression is desired only at certain times or at certain locations, or when it is desirable to titrate the level of expression using an inducing agent. Transcriptionally active elements can also be tissue-specific; that is, they exhibit activity only in certain tissues or cell types.

Transcriptionally active elements can be incorporated into an ITR in a variety of ways. In some embodiments, a transcriptionally active element is incorporated 5' to any portion of an ITR or 3' to any portion of an ITR. In other embodiments, a transcriptionally active element of a transcriptionally-activated ITR lies between two ITR sequences. If the transcriptionally active element comprises two or more elements which must be spaced apart, those elements may alternate with portions of the ITR. In some embodiments, a hairpin structure of an ITR is deleted and replaced with inverted repeats of a transcriptional element. This latter arrangement would create a hairpin mimicking the deleted portion in structure. Multiple tandem transcriptionally active elements can also be present in a transcriptionally-activated ITR, and these may be adjacent or spaced apart. In addition, protein binding sites (e.g., Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the nucleic acid molecule in a relatively limited nucleotide sequence length which effectively maximizes the length of a transgene which can be carried and expressed from the nucleic acid molecule. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicates the functional elements of the transcriptionally active element. A number of techniques exist in the art to efficiently add, delete, and/or change particular nucleotide sequences at specific sites (see, for example, Deng and Nickoloff (1992) Anal. Biochem. 200:81-88). Another way to create transcriptionally-activated ITRs involves the introduction of a restriction site at a desired location in the ITR. In addition, multiple transcriptionally activate elements can be incorporated into a transcriptionally-activated ITR, using methods known in the art.

By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ box, APBα box, CArG box, CCAC box, or any other element involved in transcription as known in the art.

II.A.3. Gene of Interest and Other Sequences

Certain aspects of the present disclosure are directed to methods of administering to a subject an AAV therapy. In some embodiments, the AAV comprises a gene of interest (GOI). In some embodiments, the gene of interest is a non-AAV gene. In some embodiments, the GOI is a mammalian gene. In some embodiments, the GOI is a human gene. In some embodiments, the gene of interest encodes a biologically active polypeptide. In some embodiments, the biologically active polypeptide is a cytokine, a chemokine, a growth factor, a clotting factor, a hormone, an antibody, insulin, or any combination thereof.

In some embodiments, the gene of interest, for example, encodes a therapeutic polypeptide or a therapeutically effective portion thereof. The gene of interest can be any polynucleotide that encodes a polypeptide. The gene being expressed can be either a DNA segment encoding a protein, with any necessary control elements (e.g., promoters, operators) that are desired by the user, or a non-coding DNA segment, the transcription of which produces all or part of some RNA-containing molecule, such as a ribozyme or an anti-sense molecule.

In some embodiments, the AAV comprises more than one GOI. In AAVs with more than one GOI, some embodiments include elements such as IRES or 2A, to co-express them from one promoter. In some embodiments, the AAV comprises two genes of interest separated by an IRES element. In some embodiments, the AAV comprises two genes of interest separated by a 2A element. In some embodiments, the AAV comprises three genes of interest separated by an IRES element between the genes of interest (e.g., GOI-IRES-GOI-IRES-GOI). In some embodiments, the AAV comprises three genes of interest separated by 2A elements between the genes of interest.

In some embodiments, the AAV comprises a regulatory sequence. In some embodiments, the AAV comprises non-coding regulatory DNA. In some embodiments, the AAV genome comprises regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, CA (1990)). It will be appreciated by those skilled in the art that the design of the AAV, including the selection of regulatory sequences, can depend on such factors as the choice of the host cell to be transformed, the level of expression of protein desired, etc. In some embodiments, the AAV genome comprises mRNA splice donor/splice acceptor sites. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Biol.* 8:466-472). In certain embodiments, the regulatory sequence comprises a tissue specific promoter. In some embodiments, the tissue specific promoter drives expression of the gene of interest in a tissue selected from the group consisting of heart, liver, lungs, eyes, nervous system, lymphatic system, muscle and stem cells.

II.B. ELISA

Certain aspects of the present disclosure are directed to methods of detecting and/or measuring the titer of an anti-AAV antibody in a biological sample using an ELISA. Any ELISA known in the art can be used in the methods disclosed herein. In some embodiments, the ELISA is a population ELISA. In certain embodiments, the ELISA is luminescent ELISA. In certain embodiments, the ELISA is a chemiluminescent ELISA.

In certain aspects of the present disclosure, the ELISA comprises binding a target AAV to a surface, e.g., the surface of a plate. In some embodiments, the ELISA then comprises contacting the AAV bound to the surface with the biological sample. In some embodiments, the ELISA then comprises applying a secondary antibody. In some embodiments, the secondary antibody is linked to an enzyme. In some embodiments, the ELISA then comprises applying a substrate, wherein substrate is specific for the enzyme linked to the secondary antibody. In some embodiments, the ELISA comprises measuring a product of the enzyme acting on the substrate.

In certain embodiments, the target AAV that is bound to the surface comprises AAV type 1, AAV type 2, AAV type 3, AAV type 4, AAV type 5, AAV type 6, AAV type 7, AAV type 8, AAV type 9, AAV type 10, AAV type 11, AAV type 12, AAV type 13, or any combination thereof. In certain embodiments, the target AAV that is bound to the surface comprises AAV type 2. In certain embodiments, the target AAV that is bound to the surface comprises rAAV type 2. In certain embodiments, the target AAV that is bound to the surface comprises AAV type 5. In certain embodiments, the target AAV that is bound to the surface comprises rAAV type 5. In certain embodiments, the target AAV that is bound to the surface comprises AAV type 9. In certain embodiments, the target AAV that is bound to the surface comprises rAAV type 9.

In certain embodiments, the biological sample is applied to the surface of the ELISA. The biological sample can be any sample obtained from a subject, wherein the sample comprises or is believed to comprise one or more anti-AAV antibody. In some embodiments, the biological sample comprises a blood sample. In some embodiments, the biological sample comprises a plasma sample. In some embodiments, the biological sample comprises a serum sample.

The biological sample can be collected and/or obtained by any method known in the art. In some embodiments, the biological sample is obtained directly from a subject, e.g., by withdrawing the sample directly from the circulatory system of a subject. In other embodiment, the biological sample is obtained from a lab, wherein the lab, or a predecessor, previously obtained the biological sample directly from a subject. In some embodiments, the biological sample is fresh, e.g., the sample has not been frozen or stored for an extended period of time. In other embodiments, the biological sample has been stored at a temperature less than 37° C.

In certain embodiments, the biological sample is diluted prior to the ELISA. In some embodiments, the biological sample is diluted by at least about 1:2, at least about 1:3, at least about 1:4, at least about 1:5, at least about 1:10, at least about 1:20, at least about 1:30, at least about 1:40, at least about 1:50, at least about 1:100, at least about 1:150, at least about 1:200, at least about 1:250, at least about 1:300, at least about 1:350, at least about 1:400, at least about 1:450, at least about 1:500, at least about 1:1000, at least about 1:2000, at least about 1:3000, at least about 1:4000, at least about 1:5000, at least about 1:10,000, at least about 1:20,000, at least about 1:30,000, at least about 1:40,000, at least about 1:50,000, or at least about 1:100,000. In some embodiments, the biological sample is diluted by at least about 1:4. In some embodiments, the biological sample is diluted by at least about 1:40. In some embodiments, the biological sample is diluted by at least about 1:400. In some embodiments, the biological sample is diluted by at least about 1:4000. In some embodiments, the biological sample is diluted by at least about 1:40,000. Any dilution buffer commonly used under these circumstances and known in the art might be used.

In certain embodiments, the biological sample is purified prior to its application to the surface of the ELISA.

In certain embodiments, secondary antibody comprises an anti-human antibody. In some embodiments, the secondary antibody comprises an anti-human λ antibody. In some embodiments, the secondary antibody comprises an anti-human κ antibody. In some embodiments, the secondary antibody comprises a combination of an anti-human κ antibody and an anti-human λ antibody. In some embodiments, the secondary antibody is a goat anti-human λ antibody. In some embodiments, the secondary antibody is a rabbit anti-human κ antibody. In some embodiments, the secondary antibody is a rabbit anti-human λ antibody. In some embodiments, the secondary antibody is a mouse anti-human κ antibody. In some embodiments, the secondary antibody is a goat anti-human λ antibody. In some embodiments, the secondary antibody is a mouse anti-human κ antibody. In some embodiments, the secondary antibody is a rat anti-human λ antibody. In some embodiments, the secondary antibody is a rat anti-human κ antibody.

In some embodiments, the secondary antibody is linked to an enzyme. The enzyme can be any enzyme used in the art for an ELISA. In some embodiments, the secondary antibody is linked to an alkaline phosphatase (AP). In some embodiments, the secondary antibody is linked to a horse radish peroxidase (HRP). In certain embodiments, the secondary antibody is a HRP-conjugated goat anti-human λ antibody. In certain embodiments, the secondary antibody is a HRP-conjugated goat anti-human κ antibody. In some embodiments, the secondary antibody comprises a combination of an HRP-conjugated goat anti-human λ antibody and an HRP-conjugated goat anti-human κ antibody.

Certain aspects of the present disclosure are directed to methods of identifying a subject having a low titer of an anti-AAV antibody using an ELISA. In some embodiments, the low titer of the anti-AAV antibody is less than about 800 to less than about 40,000. In some embodiments, the anti-AAV antibody titer is less than about 50,000, less than about 45,000, less than about 40,000, less than about 35,000, less than about 30,000, less than about 25,000, less than about 20,000, less than about 15,000, less than about 10,000, less than about 9000, less than about 8000, less than about 7000, less than about 6000, less than about 5000, less than about 4000, less than about 3000, less than about 2000, less than about 1000, less than about 900, less than about 800, less than about 700, less than about 600, or less than about 500, as measured by chemiluminescent ELISA.

In certain embodiments, the anti-AAV antibody titer is less than about 40,000, as measured by chemiluminescent ELISA. In certain embodiments, the anti-AAV antibody titer is less than about 10,000, as measured by chemiluminescent ELISA. In certain embodiments, the anti-AAV antibody titer is less than about 4000, as measured by chemiluminescent ELISA. In certain embodiments, the anti-AAV antibody titer is less than about 1000, as measured by chemiluminescent ELISA. In certain embodiments, the anti-AAV antibody titer is less than about 900, as measured by chemiluminescent ELISA. In certain embodiments, the anti-AAV antibody titer is less than about 850, as measured by chemiluminescent ELISA. In certain embodiments, the anti-AAV antibody titer is less than about 800, as measured by chemiluminescent ELISA. In certain embodiments, the anti-AAV antibody titer is less than about 750, as measured by chemiluminescent ELISA. In certain embodiments, the anti-AAV antibody titer is less than about 700, as measured by chemiluminescent ELISA. In certain embodiments, the anti-AAV antibody titer is less than about 650, as measured by chemiluminescent ELISA. In certain embodiments, the anti-AAV antibody titer is less than about 600, as measured by chemiluminescent ELISA. In certain embodiments, the anti-AAV antibody titer is less than about 550, as measured by chemiluminescent ELISA. In certain embodiments, the anti-AAV antibody titer is less than about 500, as measured by chemiluminescent ELISA. In certain embodiments, the anti-AAV antibody titer is less than about 400, as measured by chemiluminescent ELISA. In certain embodiments, the anti-AAV antibody titer is less than about 300, as measured by chemiluminescent ELISA. In certain embodiments, the anti-AAV antibody titer is less than about 200, as measured by chemiluminescent ELISA. In certain embodiments, the anti-AAV antibody titer is less than about 100, as measured by chemiluminescent ELISA.

In some embodiments, the subject is identified as having a low titer of the anti-AAV antibody if the biological sample emits less than about 100,000 chemiluminescence units in a chemiluminescence ELISA. In some embodiments, the subject is identified as having a low titer of the anti-AAV antibody if the biological sample emits less than about 100,000, less than about 50,000, less than about 45,000, less than about 40,000, less than about 35,000, less than about 30,000, less than about 25,000, less than about 20,000, less than about 15,000, less than about 10,000, less than about 9000, less than about 8000, less than about 7000, less than about 6000, less than about 5000, less than about 4000, less than about 3000, less than about 2000, less than about 1000, less than about 950, less than about 900, less than about 850, less than about 800, less than about 750, less than about 700, less than about 650, less than about 600, less than about 5500, or less than about 500 chemiluminescence units in a chemiluminescence ELISA.

In certain embodiments, the subject is identified as having a low titer of the anti-AAV antibody if the biological sample emits less than about 10,000 chemiluminescence units in a chemiluminescence ELISA. In certain embodiments, the subject is identified as having a low titer of the anti-AAV antibody if the biological sample emits less than about 4000 chemiluminescence units in a chemiluminescence ELISA. In certain embodiments, the subject is identified as having a low titer of the anti-AAV antibody if the biological sample emits less than about 1000 chemiluminescence units in a chemiluminescence ELISA. In certain embodiments, the subject is identified as having a low titer of the anti-AAV antibody if the biological sample emits less than about 900 chemiluminescence units in a chemiluminescence ELISA. In certain embodiments, the subject is identified as having a low titer of the anti-AAV antibody if the biological sample emits less than about 850 chemiluminescence units in a chemiluminescence ELISA. In certain embodiments, the subject is identified as having a low titer of the anti-AAV antibody if the biological sample emits less than about 800 chemiluminescence units in a chemiluminescence ELISA. In certain embodiments, the subject is identified as having a low titer of the anti-AAV antibody if the biological sample emits less than about 750 chemiluminescence units in a chemiluminescence ELISA. In certain embodiments, the subject is identified as having a low titer of the anti-AAV antibody if the biological sample emits less than about 700 chemiluminescence units in a chemiluminescence ELISA. In certain embodiments, the subject is identified as having a low titer of the anti-AAV antibody if the biological sample emits less than about 650 chemiluminescence units in a chemiluminescence ELISA. In certain embodiments, the subject is identified as having a low titer of the anti-AAV antibody if the biological sample emits less than about 600 chemiluminescence units in a chemiluminescence ELISA. In certain embodiments, the subject is identified as having a low titer of the anti-AAV antibody if the biological sample emits less than about 550 chemiluminescence units in a chemiluminescence ELISA. In certain embodiments, the subject is identified as having a low titer of the anti-AAV antibody if the biological sample emits less than about 500 chemiluminescence units in a chemiluminescence ELISA.

In some embodiments, the low titer of the anti-AAV antibody correlates with a low titer of neutralizing anti-AAV antibodies.

The present disclosure is further illustrated by the following examples which should not be construed as further limiting. The contents of all references cited throughout this application are expressly incorporated herein by reference.

EXAMPLES

Example 1

The present study is intended to determine if there is a correlation between the total titer of anti-AAV antibodies measured using ELISA and the titer of neutralizing antibodies measured using standard cell-based assays, with the objective of substituting the cell-based assay with the total antibody assay for patient exclusion purposes.

We developed a highly sensitive chemiluminescent plate-based ELISA detection method for anti-AAV9 antibodies. We also built a confirmatory tier into the total antibody screening method to evaluate the specificity of ELISA signals. Using this assay, over a 100 heart disease patient serum samples were analyzed for total AAV antibodies. The same samples were assessed for neutralizing antibodies in a typical cell-based reporter assay that measured the ability of the antibodies to prevent AAV binding and entry into cells.

Our results suggest a strong correlation between the total and neutralizing antibody populations for AAV serotype 9. Based on these results, we propose the use of a total antibody ELISA assay to screen and select patients receiving AAV9 based gene therapeutics.

Materials and Methods

Reagents

Serum samples were collected from consented patients at the University of Dundee, Scotland. The subjects were heart failure patients with either HFrEF (heart failure with reduced ejection fraction) or HFpEF (heart failure with preserved ejection fraction). Serum samples were procured with a material transfer agreement (MTA) contract between BMS and University of Dundee, and stored at the BMS Biorepository at −80° C. until use.

Enzyme-Linked Immunosorbent Assay rAAV9S100A1 (AMT-120; uniQure Amsterdam) or rAAV9HLuc (AAV9-CMV-Luciferase 924; uniQure Amsterdam) stocks were diluted in carbonate-bicarbonate buffer (SRE0034; SIGMA) to 2.5-5.1×10$^{11}$ titer particles/mL (approximately 4-8 µg/mL total protein concentration). 100 µL was coated on ELISA plates, and the plates were sealed with microplate sealers (WHA77040001; SIGMA) and incubated in a 4° C. refrigerator for 16-18 hours to allow for passive adsorption of AAV9 to the polystyrene surface of plates. For colorimetric ELISA, Nunc 96-well clear polystyrene plates (Thermo Fisher Roskilde, Denmark) were used. For chemiluminescent ELISAs, Corning 96-well black polystyrene plates (Corning Inc. N.Y.) were used. On the next day, the plates were washed 3× using 300 µL of PBS/0.05% Tween 20 buffer (Chata Biosystems) each time in an automated plate washer (Biotek ELx405, Winooski Vt.). 300 µL of Superblock T20 (SBT20) buffer (Thermo-Scientific) was added to the plates to block non-specific protein detection in further steps. The plates were sealed and incubated without shaking in a 22° C. incubator for 2.5-3 hours.

ADK9 anti-rAAV9 monoclonal antibody control (651162; Progen) and human serum dilutions were prepared in polypropylene plates (951031861; Eppendorf) using SBT20 buffer as the diluent. The ADK9 control antibody was used at dilutions of 1:50, 1:100, or 1:1000 as indicated in the figure legends. The serum samples were diluted to various levels as indicated in the figures. The dilutions were stored at 4° C. until use. For the competition ELISA, the ADK9 control and serum dilutions were prepared at 2× of the intended concentrations and equal amounts were mixed with 8 µg/mL of rAAV9 (competed Abs) or equal volumes of SBT20 buffer (uncompeted control) and incubated in polypropylene plates at 22° C. for 2 hours prior to use. Plates were washed as described earlier and 100 µL of diluted rAAV9 ADK9 control antibody or human serum were added to the plates. For the background controls, 100 µL of SBT20 buffer was added to control wells. In the competition ELISA, 100 µL of the competed or non-competed control rAAV9 ADK9 antibody and human serum were added to the plates.

The plates were sealed and incubated for 1.5-2 hours in a 22° C. incubator on a microplate shaker at approximately 200-250 rpm. HRP-conjugated goat anti-mouse IgA (62-6720; Thermo Scientific) detection antibody was diluted 1,000 fold and HRP-conjugated goat anti-human κ (2060-05; SouthernBiotech) and HRP-conjugated goat anti-human λ (2070-05; Southern Biotech) detection antibodies were diluted 10,000 fold in SBT20 buffer. The dilutions were stored at 4° C. until use. Plates were washed again and 100 µL of the diluted detection antibodies were added to appropriate wells including the background control wells and the plates were sealed and incubated for 45 minutes to 1.5 hours at 22° C. on a shaker. The plates were washed again and 100 µL of TMB substrate (T5569; SIGMA) was added to the colorimetric ELISA plates or 100 µL of chemiluminescent substrate (37069; Thermo Scientific) was added to the chemiluminescent ELISA plates. 100 µL of stop reagent (S5814; SIGMA) was added to the colorimetric ELISA plate and the absorbance was read at 450 nM in a Spectramax M5e plate reader (Molecular Device, Sunnyvale, CA). The chemiluminescent ELISA plates were read in the same plate reader in the luminescence setting with an integration time of 500 milliseconds.

ELISA Calculations

Signal-to-noise (S/N) in the ELISA was calculated by dividing the average chemiluminescence or absorbance units (colorimetric ELISA) obtained in the anti-AAV9 ADK9 antibody or serum incubated wells by average chemiluminescence or absorbance units obtained in the background control wells (SBT20 buffer incubation only). S/N for ADK9 entailed the units obtained with goat anti-mouse detection antibodies. S/N for human serum entailed the units obtained with goat anti-human κ and anti-human λ detection antibodies.

The percent inhibition of antibody binding to rAAV9 coated on ELISA plates when competed in solution with rAAV9 (competition ELISA) was calculated using the following formula: 100×{(average uncompeted chemiluminescence units-average competed chemiluminescence units)/average uncompeted chemiluminescence units}.

Graphing and Statistical Analysis

All graphs were generated using the GraphPad Prism v 7.03 software. Rank-order based Spearman correlative analysis of the total ELISA antibodies and neutralizing antibodies was also done using the same software. A two-tailed P value and 95% confidence interval were computed in the correlative analysis.

Neutralizing Antibody Assay

Lec-2 cells (CRL 1736; ATCC) were cultured overnight in 96-well plates at 37° C./5% CO2 in 10% FBS (Catalog #10438; Gibco) containing MEM medium (M8042; Millipore SIGMA) supplemented with 1% penicillin and streptomycin (Catalog #15140122; ThermoFisher Scientific) and 2 mM L-Glutamine (Catalog #25030081; ThermoFisher Scientific) at a density of 20,000 Lec-2 cells/well. The next day rAAV9HLuc stock was diluted in FBS-free MEM medium to 22,500 MOI and incubated with human serum samples diluted 20-fold with FBS-free MEM medium at room temperature for 1 hour. A negative control consisted of rAAVHLuc mixed with heat-inactivated FBS alone. Culture medium was aspirated from the Lec-2 cells and 100 µL of the AAV9 and serum mixture or control was added to the cells and incubated for 30 minutes at 37° C./5% CO2. The medium was replaced with 10% FBS-DMEM and the cells were incubated for 16-20 hours at 37° C./5% CO2. Following removal of medium and a 100 µL 1×DPBS (Catalog #14190094; Invitrogen) wash, cells were lysed using 100 µL of GLO lysis buffer (E2661: Promega) and incubated at room temperature for 5 minutes. 100 µL luciferase substrate (E6120; Promega) were prepared according to manufacturer's instructions and added to the lysed cells and incubated for 3 minutes. The luminescence signal was measured using a plate reader (Enspire; Perkin Elmer). The neutralizing activity of the serum samples is reported as a percentage of the negative FBS control (% FBS).

Results

Figures 3A, 3B:
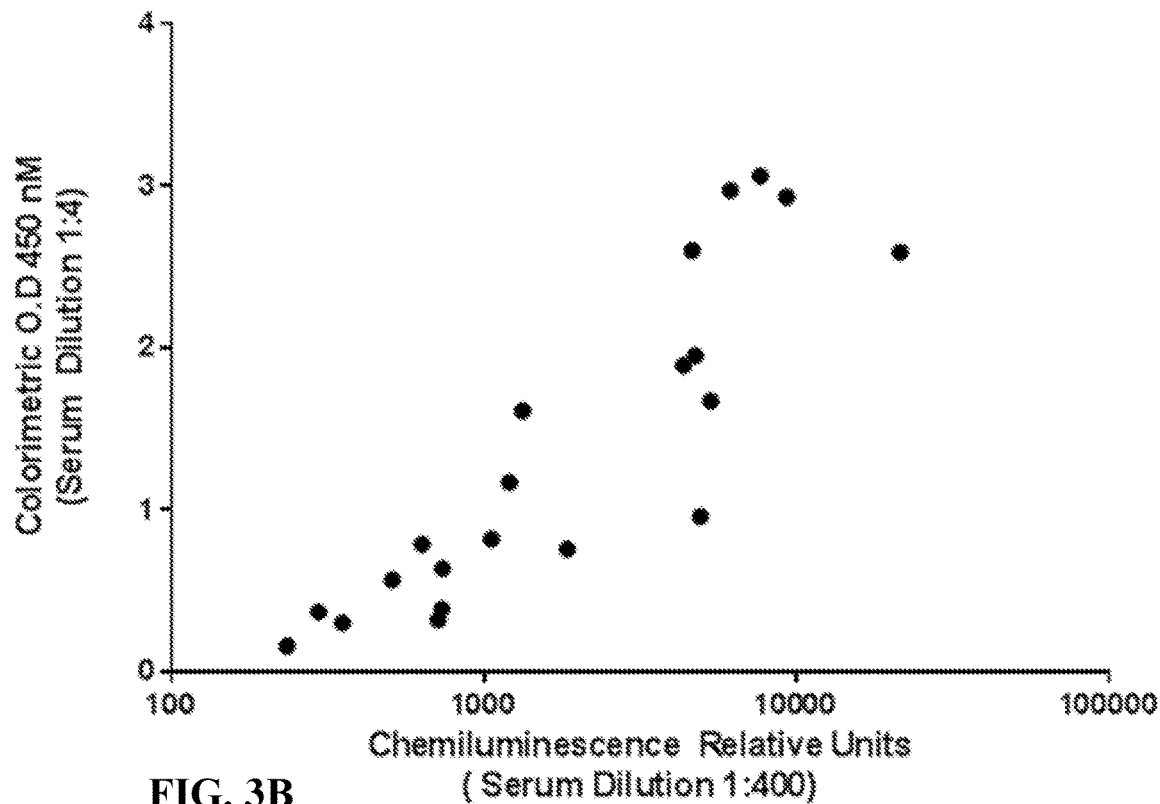
FIG. 3A is a scatter plot showing the correlation between the chemiluminescent and colorimetric detection methods.
FIG. 3B provides the statistical analysis of the data presented in FIG. 3A.

Comparison of Chemiluminescent and Colorimetric ELISA Detection Methods for Total Anti-AAV9 Antibodies Using a Mouse Monoclonal Antibody Control Colorimetric ELISAs have previously been used to detect anti-AAV Abs. Given the superior sensitivity of chemiluminescent ELISAs in detecting protein specific antibodies in general, we compared the two methods for anti-AAV antibody detection. Clear or black polystyrene plates were coated with AAV9 capsids containing either the transgene for luciferase (rAAV9-HLuc) or S100A1 (rAAV9-S100A1) at a concentration of 8 µg/mL in carbonate buffer overnight and detected with ADK9, a mouse monoclonal anti-AAV9 antibody as described in the methods section. The rAAV9-HLuc particles contain the fire-fly luciferase reporter construct used in the cell-based neutralizing antibody assay. Although both AAV9 particles were constructed to have identical capsids, the luciferase capsid was included in the ELISA to demonstrate capsid similarity and to enable correlative interrogations of the total and neutralizing antibody data sets. As shown in table 1, at dilutions of 1:50 and 1:100 ADK9, and for both the luciferase and transgene containing constructs, the chemiluminescent ELISA showed a 21-38 fold improvement in signal-to-noise (S/N) ratio compared with the colorimetric ELISA. There were no differences in the detection of rAAV9-S100A1 and rAAV9-luciferase, demonstrating that the AAV9 capsids were similar in terms of antibody reactivity.

method (FIGS. 1A-1B). A significant correlation was observed between the two methods (FIG. 3), indicating a correlative increase in sensitivity of the chemiluminescent ELISA detection method over the colorimetric method for all tested samples.

Confirmation of Anti-rAAV9 Antibody Binding Specificity in the Chemiluminescent ELISA

TABLE 1

Comparison of colorimetric and chemiluminescence ELISA detection methods for anti-rAAV9 antibodies using a mouse monoclonal antibody control. The ADK9 control was diluted 50- or 100-fold in SBT20 buffer and used to detect rAAV9-S100A1 or rAAV9-HLuc in the colorimetric or chemiluminescent ELISA methods. Signal-to-noise was calculated using the average of triplicates for ADK9 and control wells as described in the materials and methods section.

| rAAV9 Construct Type | Colorimetric | | | | Chemiluminescence | | | | Ration of S/N (Chemiluminescence/ Colorimetric) | |
|---|---|---|---|---|---|---|---|---|---|---|
| | S/N | | % CV | | S/N | | % CV | | | |
| | 1:50 | 1:100 | 1:50 | 1:100 | 1:50 | 1:100 | 1:50 | 1:100 | 1:50 | 1:100 |
| rAAV9S100A1 | 67.6 | 53.5 | 2.5 | 3.7 | 2572 | 1103 | 7.4 | 4.6 | 38 | 21 |
| rAAV9HLuc | 64.8 | 53.4 | 3.8 | 0.5 | 2385 | 1121 | 9.4 | 1.8 | 37 | 21 |

S/N = Signal-to-noise ratio

Figure 11A:
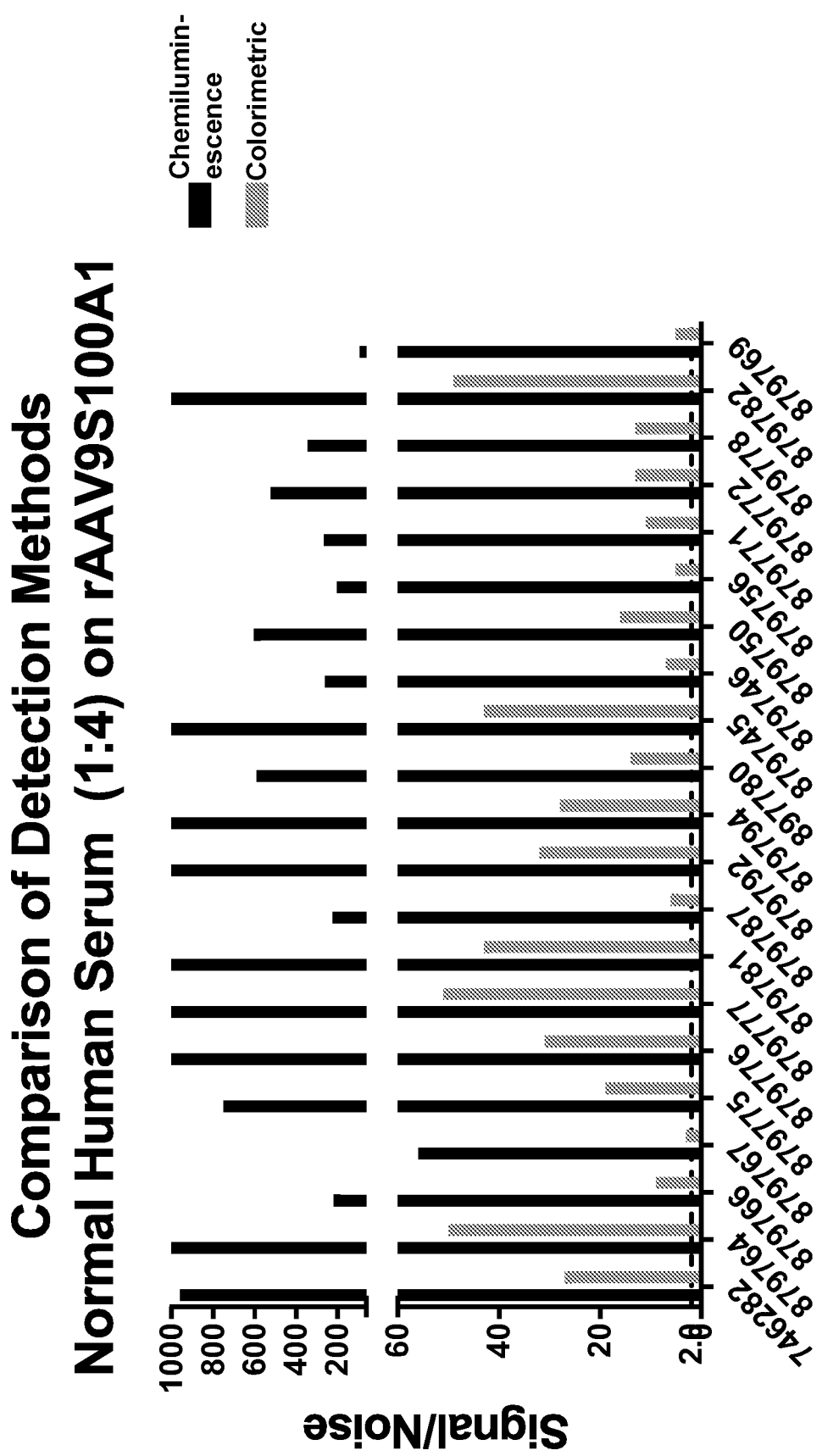
FIGS. 11A-11B are bar graphs, representing comparisons of signal-to-noise ratios for chemiluminescence (black bars) and colorimetric (grey bars) ELISA detection methods. Chemiluminescence or absorbance units at 4-fold (FIG. 11A) and 40-fold (FIG. 11B) serum dilution were obtained using anti-κ and anti-λ detection antibodies and divided by data units obtained with only SBT20 buffer incubation and anti-κ and anti-λ detection antibodies on rAAV9 coated plates.
Figure 11B:
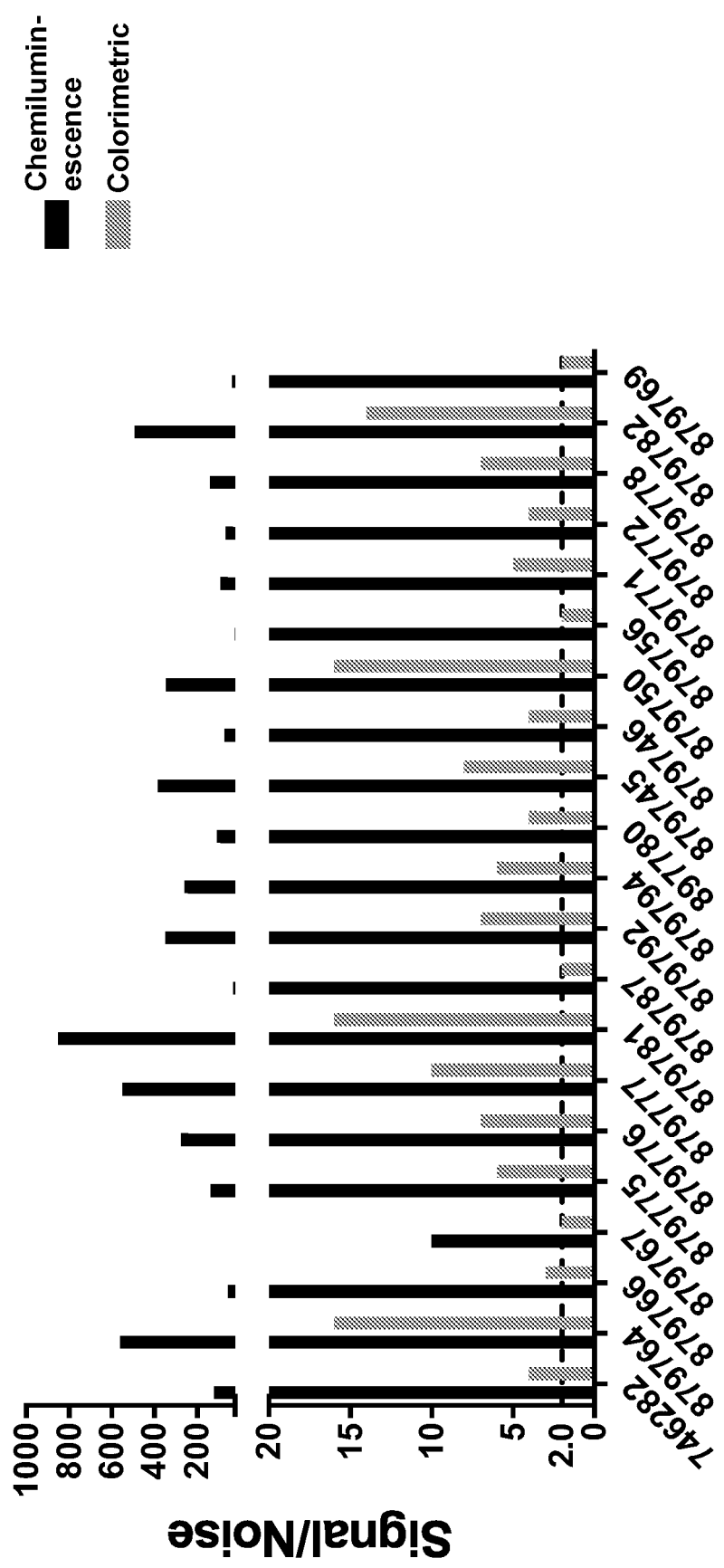

Evaluation of the Chemiluminescent ELISA for the Detection of Total Anti-AAV9 Antibodies in Human Serum Samples To ensure that the conditions determined using the mouse monoclonal control above applied to detection of human anti-AAV9 antibodies, the two ELISA detection methods were re-evaluated using commercially acquired normal human serum (NETS) samples. The plates were coated with 4 µg/mL of rAAV9S100A1 following a coating optimization experiment (data not shown). Ten-fold dilutions of eight different lots of NHS samples were prepared starting at a 4-fold dilution using SBT20 buffer. Aliquots of the dilutions were split into duplicates and tested in the chemiluminescent and colorimetric detection methods using HRP-conjugated anti-κ and anti-λ detection antibodies. In the chemiluminescence method, linearity was observed from a 4-fold to 4000-fold dilution range (FIG. 1A), whereas in the colorimetric method, linearity was detected up to a 400-fold dilution range (FIG. 1B). Thus the chemiluminescence method shows an improvement in the dynamic range of at least one log. Signal-to-noise ratio (S/N) was calculated at serum dilutions of 1:4, 1:40 and 1:400 as described in the methods section since all three dilutions fall in the approximate linear range for both methods. As a representative comparator, the S/N calculations at the 1:400-fold dilution are shown (FIG. 2). In all tested samples, the S/N was higher in the chemiluminescent method compared with the colorimetric method (FIG. 2). In all tested samples, the S/N was higher in the chemiluminescent method compared with the colorimetric method (FIG. 2). 17/21 samples showed an S/N>4.0 in the CL method whereas only 1/21 samples showed an S/N>4.0 in the colorimetric method. S/N comparisons at 1:4 and 1:400 fold serum dilutions are shown in FIG. 11A and FIG. 11B.

Figure 4A:
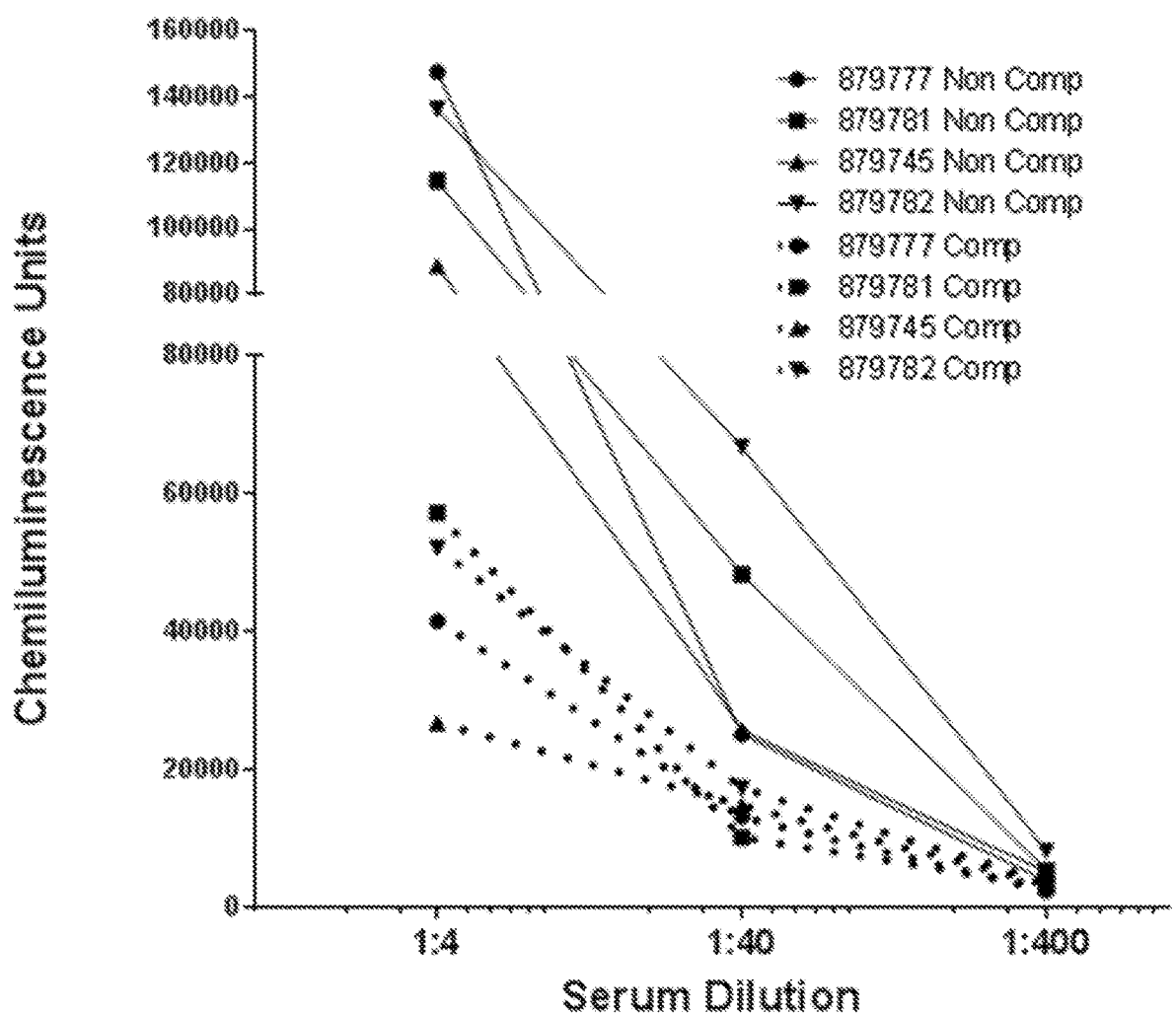
FIGS. 4A-4C are graphical representations of the results of competition of anti-rAAV9S100A1 antibody binding in the chemiluminescent ELISA. Four different normal human serum samples were diluted and three replicates of each dilution were tested with (Comp) and without (Non Comp) pre-incubation with rAAV9 in solution (FIG. 4A).
Figure 4B:
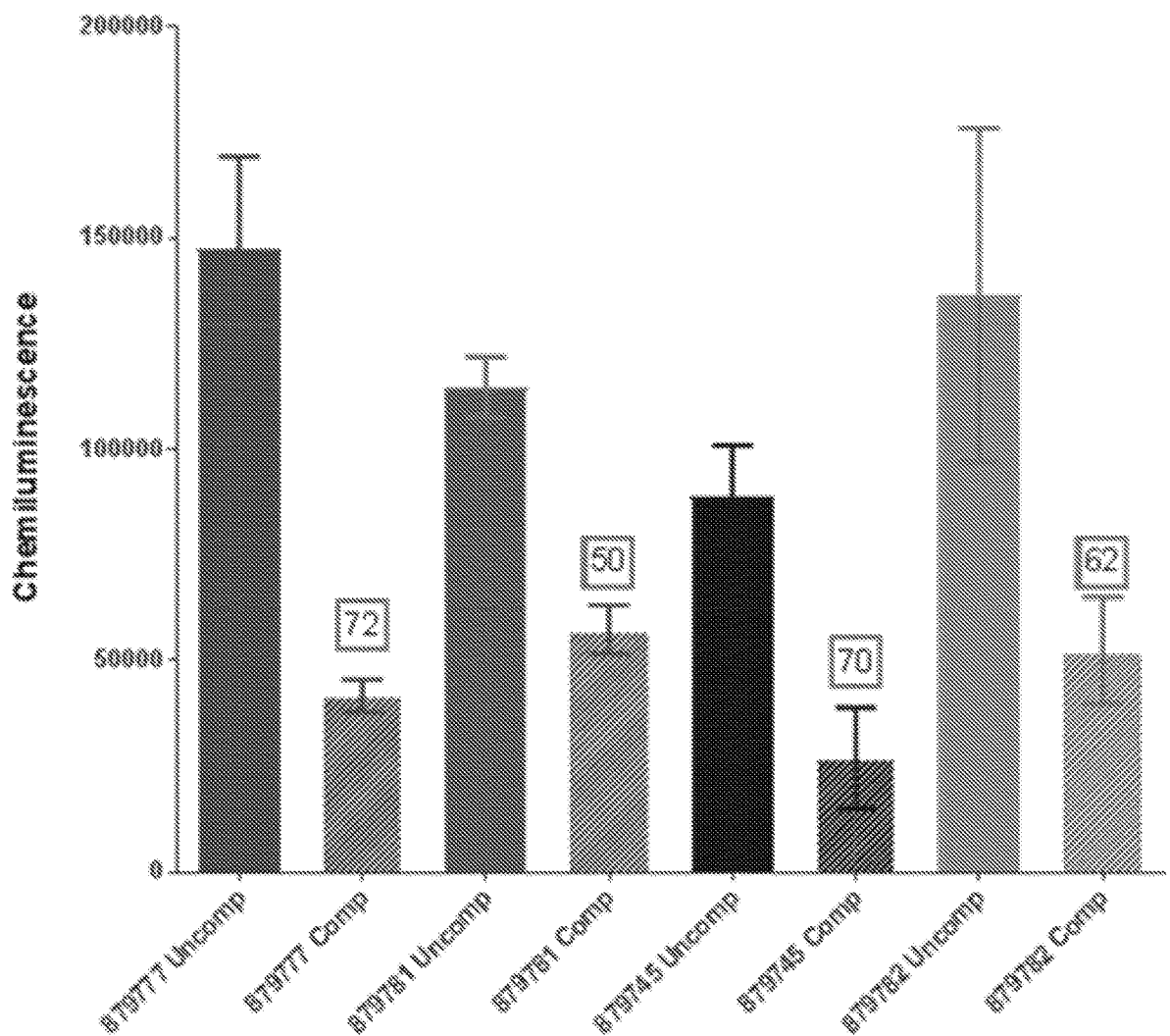
Figure 4C:
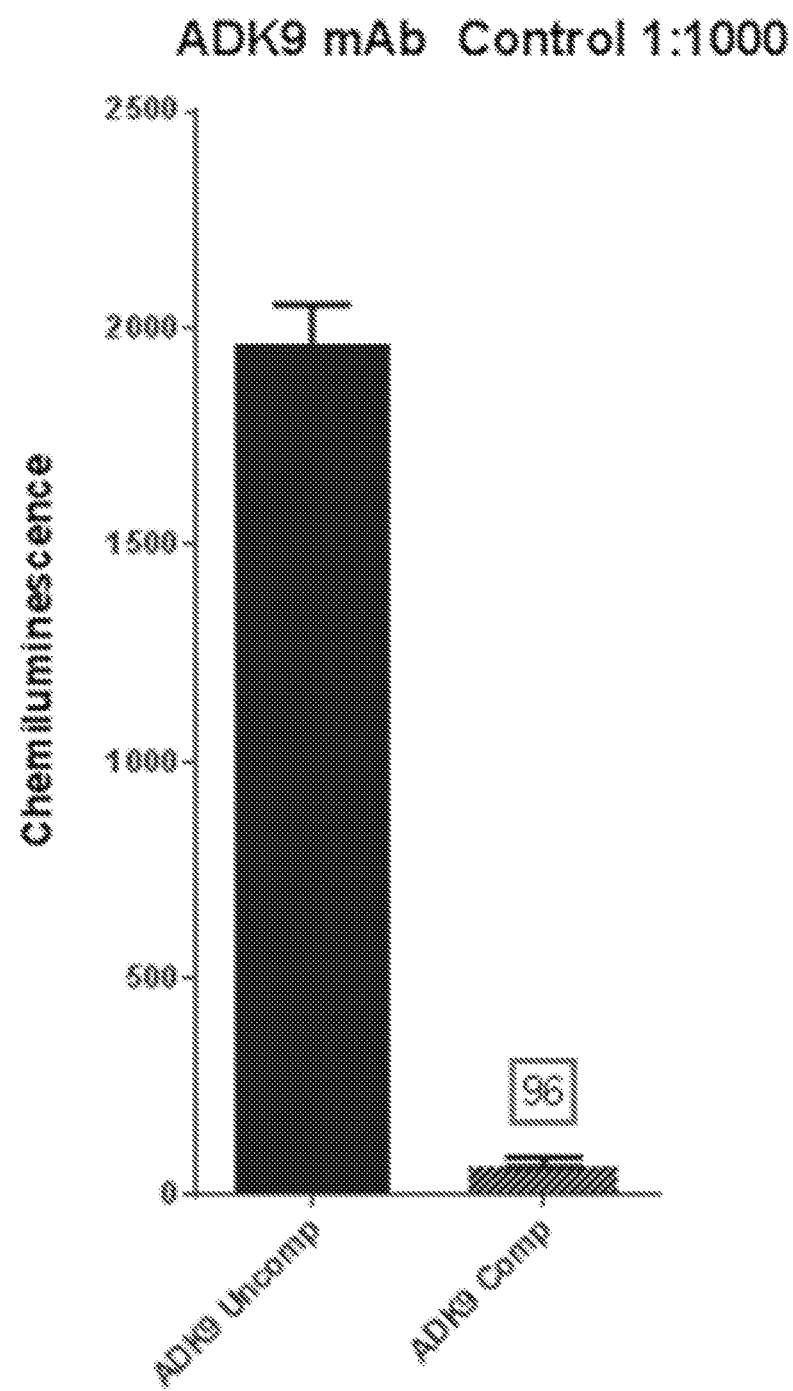

To further analyze the feasibility of using a chemiluminescent ELISA, a rank-order based non-parametric correlation analysis was done using data acquired in the colorimetric ELISA at a 4-fold serum dilution and in the chemiluminescent ELISA at a 400-fold serum dilution. The serum dilutions were selected from the linear range for each A specificity tier was introduced to the chemiluminescent ELISA to ensure that AAV9 specific antibodies, rather than non-specific serum components that bind the plate directly were being detected. Normal human serum samples were prepared at 2× of the concentrations shown and pre-incubated with 8 µg/mL rAAV9S100A1 (4 µg/mL final concentration) in polypropylene plates for two hours prior to addition of the serum samples to the washed and blocked rAAV9S100A1 coated plates (FIGS. 4A-4C). Antibodies that remained bound to the competing AAV9 capsid in solution were expected to be washed off in the ELISA following incubation on rAAV9S100A1 coated plates. The level of competition or antibody binding specificity for the plate-coated AAV9 capsid was calculated as described in the materials and methods and expressed as percent inhibition of the ELISA signal. Using this method, the four tested serum samples showed 50% or greater inhibition in the competition ELISA (FIGS. 4A-4B). The mouse ADK9 monoclonal antibody control showed an inhibition of 96% indicating that the competition parameters were optimal for near maximal levels of inhibition and specificity determination.

Reproducibility of the Chemiluminescent ELISA Method

Figure 5A:
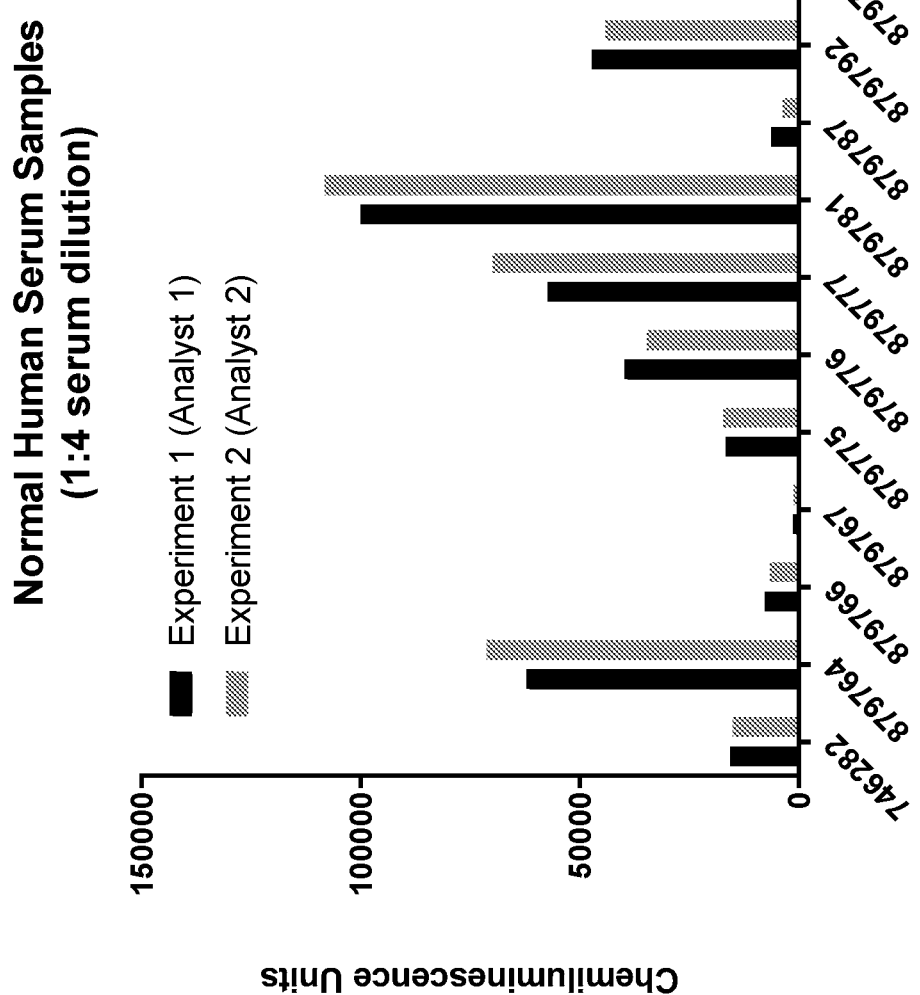
FIGS. 5A-5B are graphical representations illustrating the reproducibility of anti-AAV9 antibody detection in the chemiluminescent ELISA method. Twelve different normal human samples were diluted 40-fold (FIG. 5A) or 400-fold (FIG. 5B) and tested in two different experiments for total anti-AAV9 antibodies. The tables (FIGS. 5A and 5B) show the inter-experimental precision for each sample at respective dilutions.
Figure 5B:
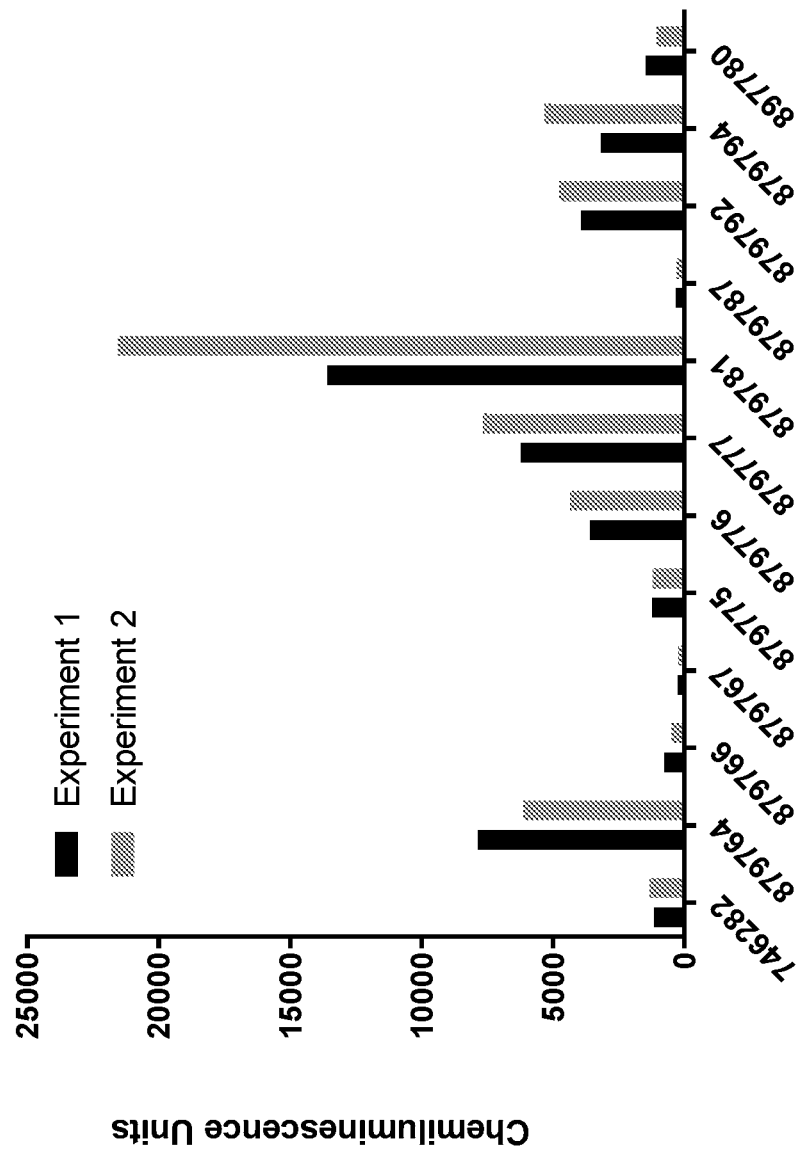

Twelve different lots of normal human serum were tested in the chemiluminescent ELISA method on two different days, each time by a different analyst to determine the reproducibility of the method (FIGS. 5A-5B). Two serum dilutions in the linear range (see FIGS. 1A-1B) were selected in the experiments. The results indicate good reproducibility between analysts at both tested dilutions and an inter-experimental precision below 30% (FIGS. 5A-5B).

Interchangeability of the Transgene and Luciferase Containing Constructs

Figure 6A:
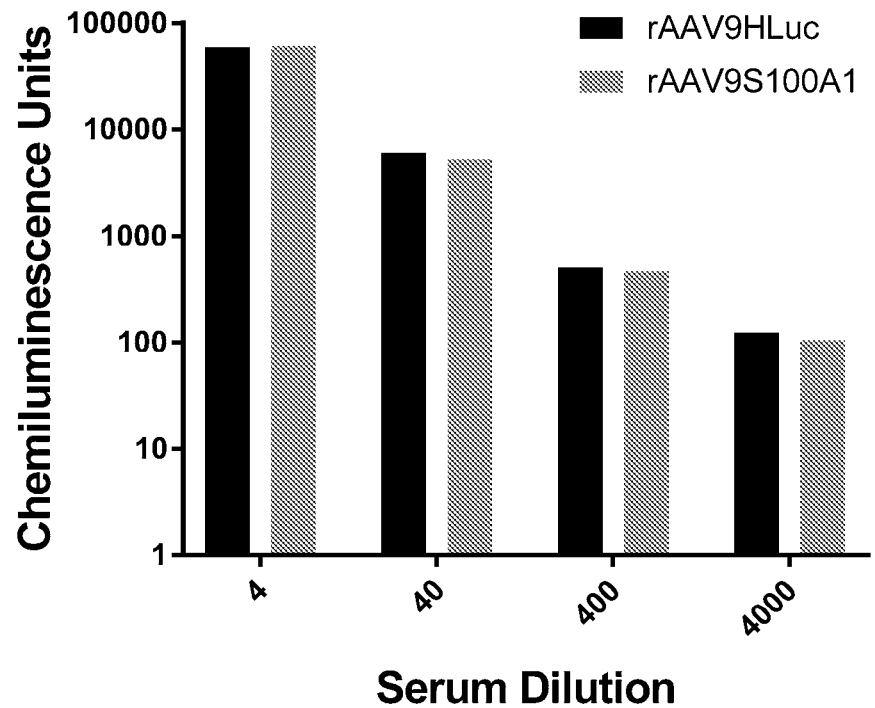
FIGS. 6A-6C are bar graphs illustrating the interchangeability of the transgene (rAAV9S100A1; grey bars) and luciferase reporter (rAAV9HLuc; black bars) containing rAAV9 capsids. Each capsid type was coated at equal concentrations and detected with serial dilutions of three different lots (FIGS. 6A-6C) of normal human serum (NHS) samples in the chemiluminescent total antibody binding ELISA as described in materials and methods.
Figure 6B:
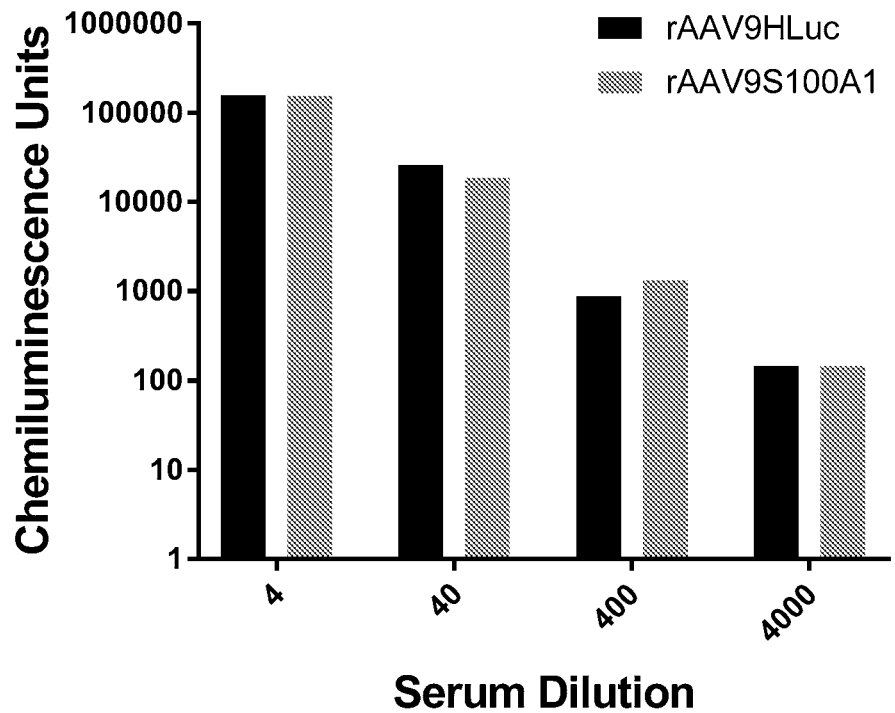
Figure 6C:
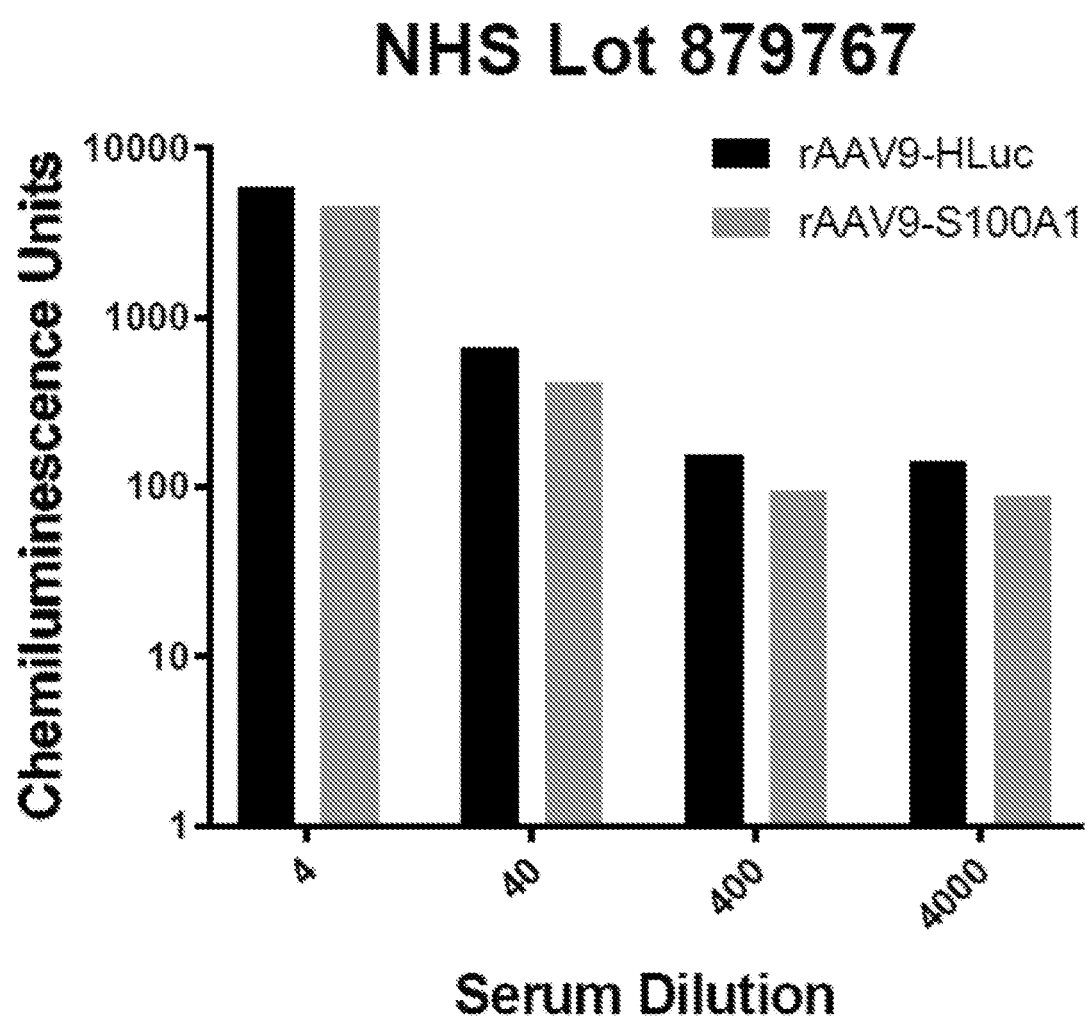

The eventual objective was to determine if there was a correlation between anti-rAAV9 total antibodies and neutralizing antibodies in a pre-screen of serum samples from a heart disease population. The total antibody assay however makes use of the rAAV9 capsid encapsulating the S100A1 transgene whereas the neutralization antibody assay makes use of the rAAV9 capsid encapsulating a luciferase reporter. To ensure that any non-correlation observed between the two data sets was not due to differences in the AAV9 capsid material used in each assay, both constructs were initially tested in the total antibody ELISA using three different lots of normal human serum as positive controls. Equal amounts of the luciferase and transgene containing rAAV9 capsids were coated on the ELISA plates and four dilutions of three different lots of normal human serum samples were used to probe the blocked and washed ELISA plates. Both capsids showed similar signals when probed with all three serum samples and at all tested dilutions (FIGS. 6A-6C). Thus, potential lack of correlation between the total and neutralizing antibody assay data would not be due to unforeseen variations in the antibody binding epitopes between the two capsid types.

Correlative Analysis of Total and Neutralizing Anti-rAAV9 Antibodies in Heart Disease Serum Samples Having demonstrated that the capsids used in the two assays, i.e., cell-based neutralizing antibody and total antibody ELISA were similar in terms of immunoreactivity, we proceeded to evaluate the correlation of neutralizing antibody data with the total antibody data on a panel of one hundred serum samples from heart disease patients. For the cell-based assay, serum samples were diluted 20-fold and incubated with the rAAV9-HLuc capsid for 1 hour and added to Lec-2 cells in culture. Controls consisting of the HLuc capsid alone or the mouse monoclonal antibody ADK9. The cells were then washed, luciferase substrate was added and the assay was completed as described in materials and methods.

The neutralizing potential of the antibodies was expressed as a percentage of the transduction of rAAV9HLuc observed in the presence of the FBS negative control (contains no anti-rAAV9 neutralizing antibodies). Since incubation of rAAV9HLuc with the negative control is expected to result in maximal cellular entry of the capsid followed by luciferase expression, a decrease in luciferase expression levels in the presence of any of the serum samples is indicative of the presence of neutralizing antibodies in the samples.

Figure 7:
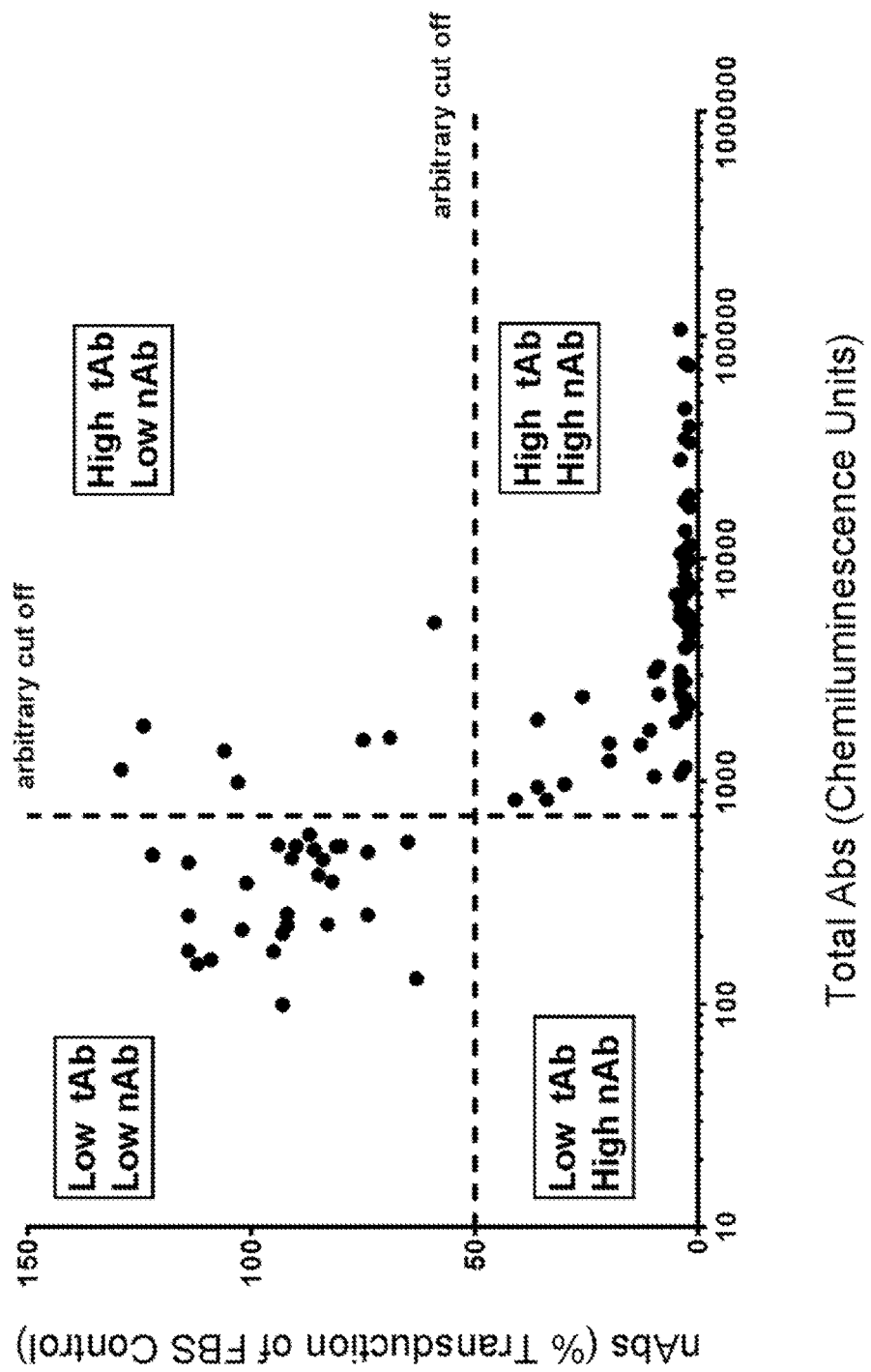
FIG. 7 is a scatter plot illustrating the correlation between total anti-AAV9 and neutralizing antibodies in heart disease patient serum samples. One hundred patients were evaluated for total binding antibodies at a serum dilution of 1:400 and neutralizing antibodies at a dilution of 1:10 and correlated using the Spearman rank-ordering method. Arbitrary cut-offs shown by the broken lines are set for each assay.

The same samples were diluted 400-fold (linear range of the assay) and evaluated for total antibodies in the ELISA as described in materials and methods. ELISA data was plotted based on raw data units. Rank-order based Spearman correlative analysis between the two data sets showed a significant negative correlation (r −0.8286, p<0.0001) between neutralizing and total antibodies (FIG. 7, p value <0.0001). An arbitrary but widely-used neutralization cut-off criteria of 50% identified 65 of 100 samples as neutralizing antibody-positive. In the total antibody ELISA, all neutralizing antibody positive subjects showed >700 chemiluminescence units (FIG. 7). A cut-off of 700 chemiluminescence units in the total antibody assay also captures 7 additional neutralizing antibody-negative individuals as shown in the upper right quadrant (FIG. 7).

Figure 8:
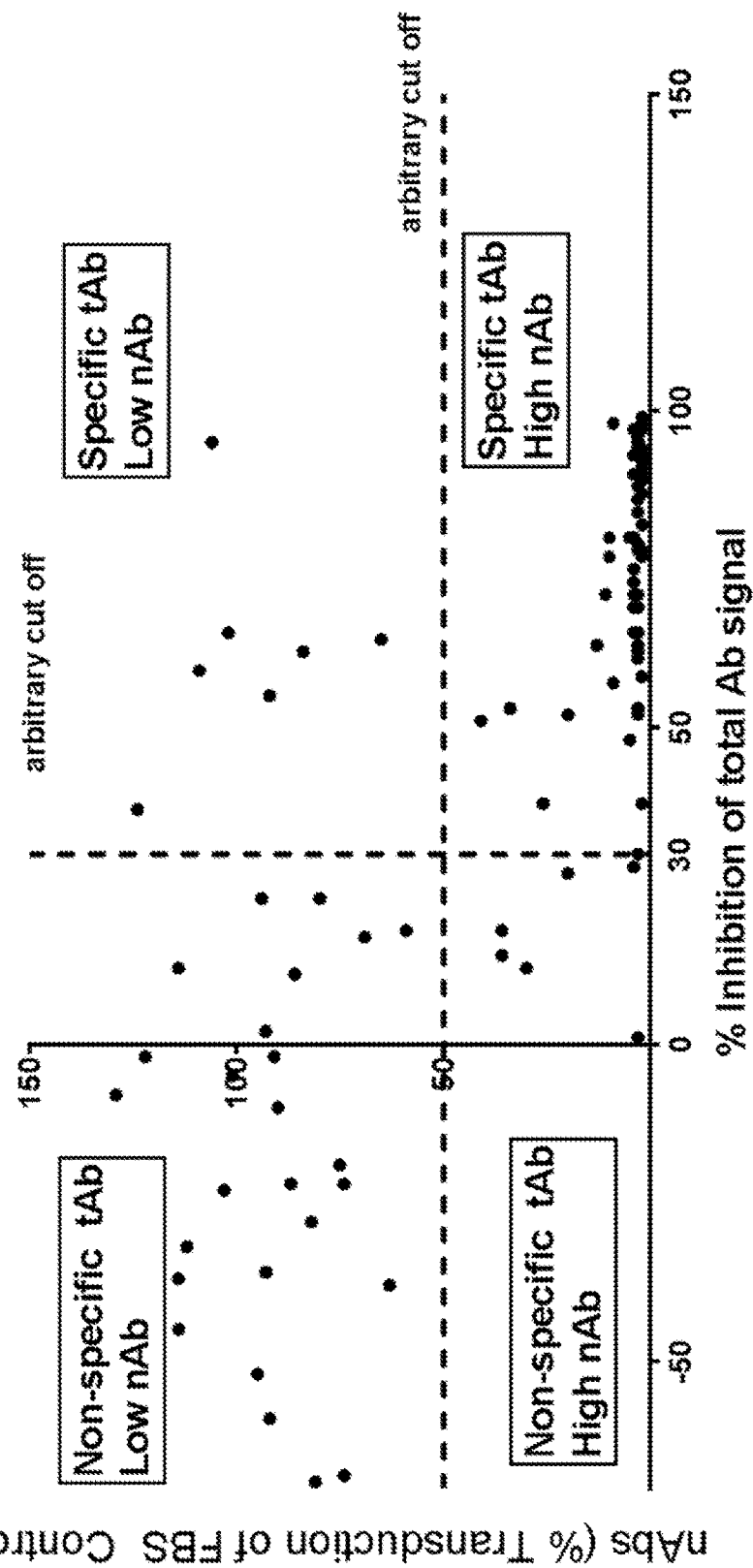
FIG. 8 is a scatter plot illustrating the correlation between total anti-AAV antibodies and AAV9 neutralizing antibodies in heart disease patient serum samples. One hundred patients were evaluated for AAV specific antibodies at a serum dilution of 1:400 post competition with AAV9 in an ELISA and neutralizing antibodies at a dilution of 1:10 in the cell-based neutralizing antibodies assay and correlated using the Spearman rank-ordering method. Arbitrary cut-offs shown by the broken lines are set for each assay.

A confirmatory or competitive ELISA was also conducted on all 100 subjects in parallel with the non-competitive ELISA as described in the materials and methods. Rank-ordered correlative analysis between the neutralizing antibody and confirmative ELISA antibody data sets also resulted in a significant negative correlation (r −0.7193, p<0.0001). Out of 65 neutralizing antibody-positive subjects, 7 individuals had antibodies with 30% or lower inhibition levels in the competitive total antibody ELISA (FIG. 8, lower left quadrant). 7 additional neutralizing antibody-negative subjects were identified as having specific antibodies in the ELISA at the arbitrary cut-off of 30% (FIG. 8, upper right quadrant).

Figure 9:
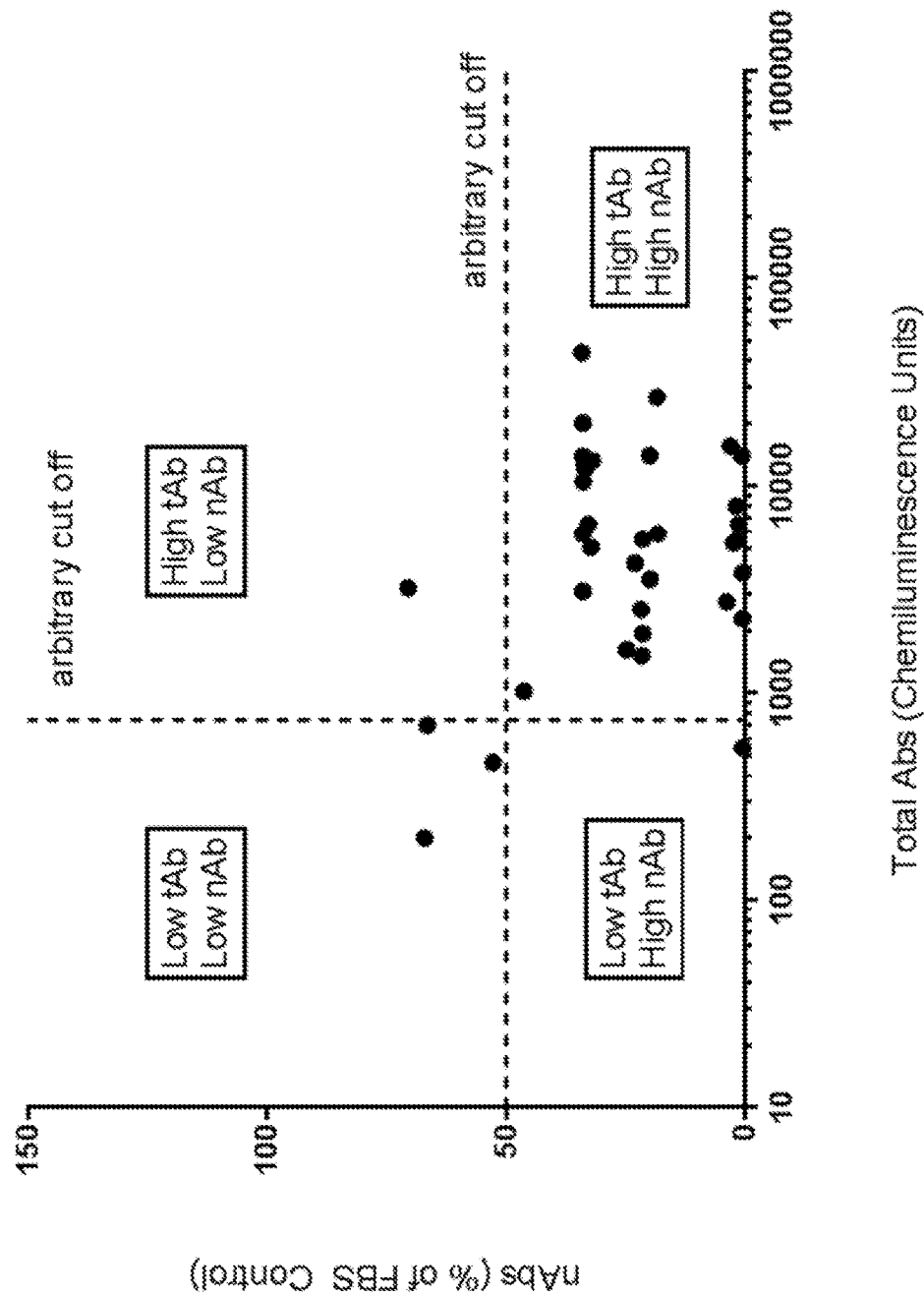
FIG. 9 is a scatter plot illustrating the correlation between total AAV type 2-binding antibodies and neutralizing antibodies in heart disease patient serum samples. Thirty-six patients were evaluated for AAV specific antibodies at a serum dilution of 1:400 in the ELISA and for neutralizing antibodies at a dilution of 1:10 in the cell-based neutralizing antibodies assay. Arbitrary cut-offs shown by the broken lines are set for each assay.

Results similar to those observed for anti-AAV type 9 antibodies were observed in results for anti-AAV type 2 antibodies (FIG. 9).

Figure 10:
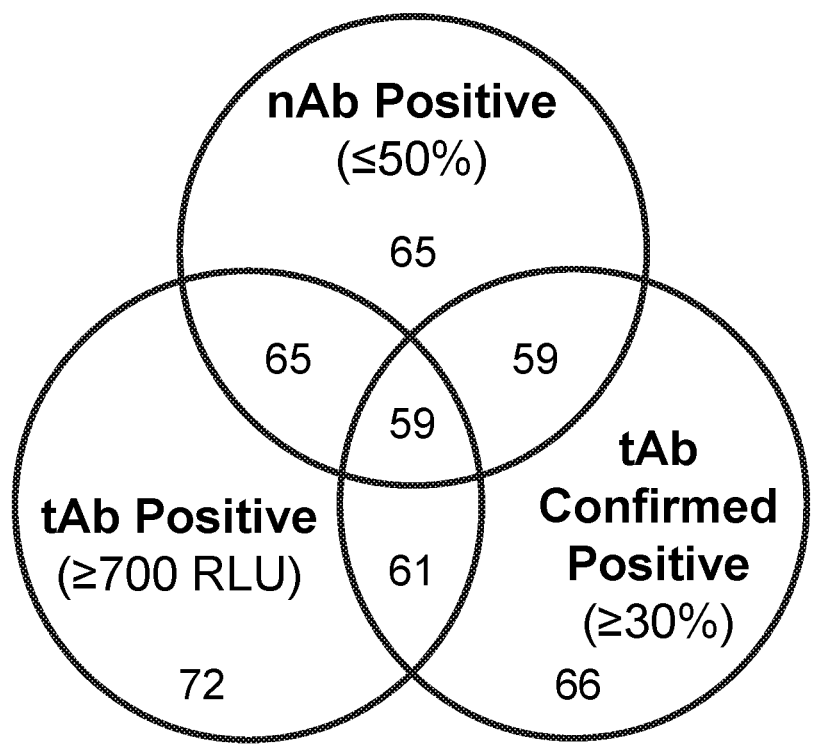
FIG. 10 is a non-scaled Venn diagram depicting the relationship between AAV9 neutralizing, total anti-AAV9, and specific (based on competition step, see Examples) total anti-AAV9 antibodies in one hundred patient samples. Arbitrary cut-offs are depicted within parentheses for each data set. The cut-off for the total antibody (tAb) data set was based on the division of a neutralizing and non-neutralizing population in the cell-based neutralizing antibody assay.

The overall statistics indicate that the number of patients excluded in the cell-based neutralizing assay and confirmed total antibody ELISA are close (65 vs. 66) (Table 2). In the total antibody ELISA, 7 or 6 additional subjects would be excluded relative to the neutralizing antibody assay and confirmatory ELISA, respectively. The three data sets were examined carefully for overlaps to determine the appropriateness of using any one of the three assays for patient screening and exclusion. These assessments were based on the arbitrary cut-offs of ≤50% for the neutralizing antibody assay, ≥700 units in the screening or total antibody ELISA and ≥30% in the confirmatory antibody ELISA. A neutralizing assay-only criteria would entail the exclusion of 6 subjects whose antibodies do not confirm positive in the ELISA (FIG. 10). Selection of patients based on the total antibody ELISA-only criteria would exclude 7 subjects who are not part of the neutralizing antibody population (neutralizing antibody false positives) and 11 subjects who are not confirmed positive in the ELISA. Selection of patients based on the confirmatory total antibody ELISA would include 6 subjects who are positive in the neutralizing antibody assay.

TABLE 2

Patient exclusion and selection statistics for each of three assays.

| Assay | Arbitrary Cut Off for Exclusion | Number of Patients Screened | Number of Patients Excluded | Number of Patients Selected |
|---|---|---|---|---|
| Cell-based Neutralization | ≤50% | 100 | 65 | 35 |
| Total Antibody ELISA | ≥700 Units | 100 | 72 | 28 |
| Confirmatory Total Antibody ELISA | ≥30% | 100 | 66 | 34 |

A correlative analysis with respect to AAV2 was carried out using the serum from 36 individual heart disease patients in the same way the correlative analysis with respect to AAV9 described herein was carried out (see Methods and FIG. 7), except that AAV2 capsid was used in the ELISA and neutralizing antibody assay and anti-AAV2 antibodies were detected rather than anti-AAV9 antibodies (see FIG. 9).

Detection of rAAV9 antibodies via HRP-conjugated anti-λ and anti-k antibodies was compared with detection via HRP-conjugated anti-IgG antibodies. rAAV9S100A1 was coated at 4 µg/mL and the ELISA was conducted as described in materials and methods using a 1:400 fold dilution of the normal human serum lots shown. Peroxidase conjugated goat anti-human IgG (A6029 SIGMA) at 1:10,000 dilution was used.

Discussion

Humans become exposed to wild-type AAV early in life and develop anti-AAV antibodies. AAV vectors derived from serotypes 1 to 9 are the most commonly used serotypes in non-clinical and clinical studies. Such pre-existing anti-AAV antibodies represent a limitation for the in vivo application of recombinant adenoviruses for gene therapy as evident in a variety of experimental outcomes. For example, passive immunization of non-clinical models with purified human IgG prior to administration of an AAV8 vector encoding a coagulation factor IX transgene was shown to block transduction of the liver (Mingozzi et al., 2012). In another study involving sequential administration of AAV serotypes in mice or non-human primates, neutralizing antibodies generated in response to one serotype totally inhibited transduction by the same serotype but did not inhibit transduction by a different serotype (Majowicz et. al., 2014). Differences in relative titers of anti-AAV2 neutralizing antibodies were reported as having potentially contributed to the prevention of a hemophilia B transgene transduction in human clinical trials (Manno et. al., 2006). In light of these observations, the identification and exclusion of clinical trial subjects and patients with pre-existing AAV antibodies may increase the chances of successful transduction of the transgene.

In general, AAV neutralizing antibodies that prevent viral attachment to cell-surface receptors and subsequent entry into host cells are detected in patient serum samples using in vitro cell-based assays and non-standardized assay conditions and identification criteria. Neutralizing antibody assays usually employ AAV viral capsids that contain a reporter gene (usually luciferase) instead of the transgene to enable an assay read-out. Cell-based assays are laborious, low throughput and prone to variation. A fair amount of assay optimization is involved for each AAV serotype under consideration, including the selection of a cell line expressing appropriate receptors that are similar to the targeted endogenous host cell receptor. In comparison, ELISAs have higher throughput, are less variable and easier to develop, automate and validate. In addition, the AAV gene therapeutic can be used directly as a reagent for plate coating and detection of anti-AAV antibodies in ELISAs. If a correlation can be demonstrated between cell-based neutralizing antibodies and total or binding antibodies detected in the ELISA, the latter can be used to identify and exclude individuals with pre-existing AAV antibodies from clinical trials and drug administration.

We sought to understand the frequency of pre-existing antibodies, both neutralizing and total in a population of patients, and then to establish a strong correlation if any, between cell-based neutralizing data and total antibody data. As a first step towards this goal, we undertook the development of a highly sensitive and specific chemiluminescent ELISA for the detection of anti-AAV9 antibodies. Due to the lack of a purified human anti-AAV antibody positive control, we used a commercial mouse monoclonal AAV9 antibody (ADK9) for initial assay development and optimization including parameters such as viral particle coating concentration, coating buffer (PBS vs. $CaCO_3$), block buffer and number of wash cycles with PBS-Tween (data not shown).

Figure 12:
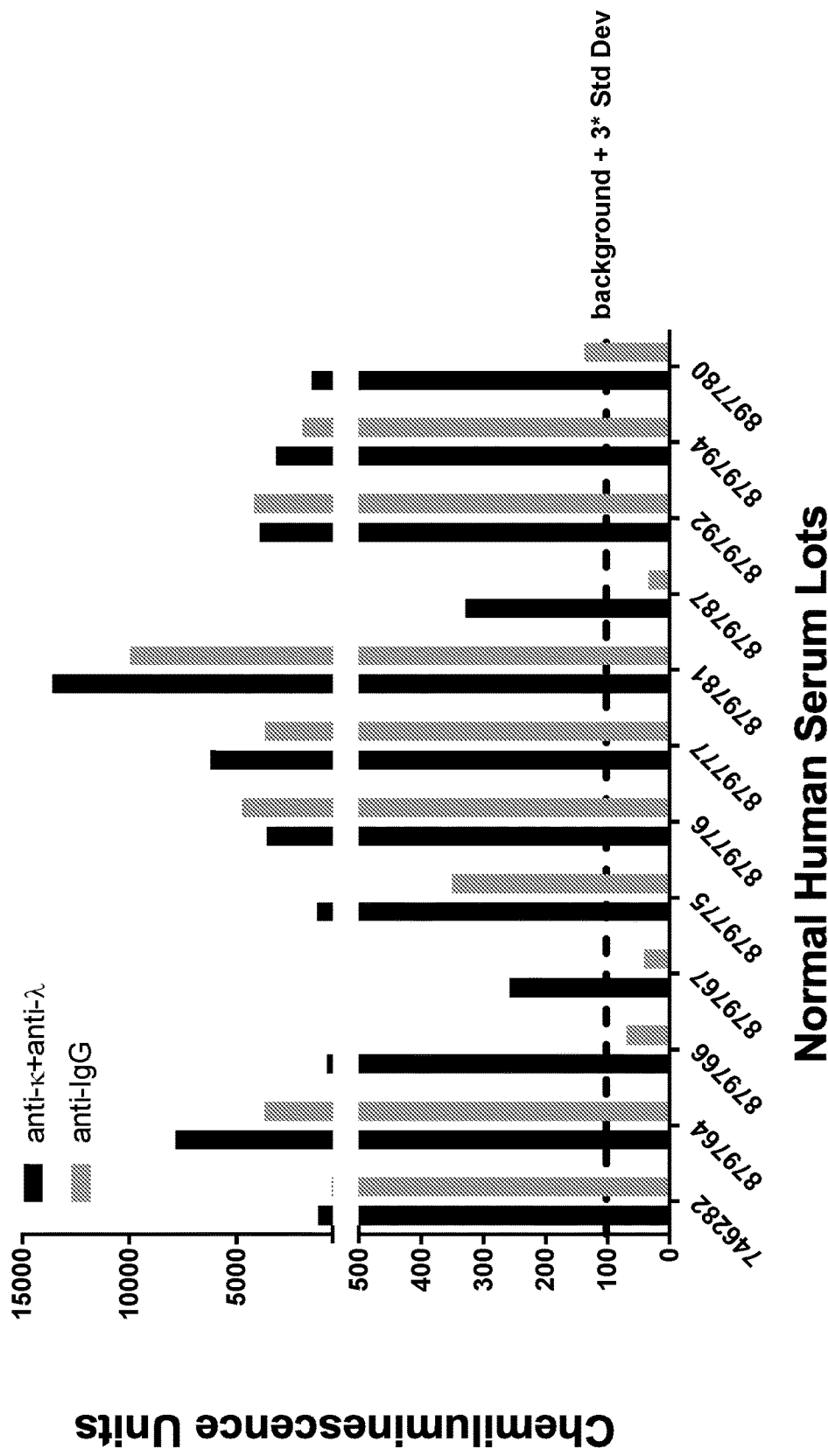
FIG. 12 is a bar graph representing a comparison of HRP-conjugated anti-κ and anti-λ detection with HRP-conjugated anti-IgG detection of rAAV9 Abs.

Several commercially available serum samples from normal healthy human donors were subsequently used to demonstrate a wide dynamic assay range and linearity (approximately 4 logs of serum dilution), reproducibility and precision. A confirmatory or specificity tier was built into the assay by pre-incubating serum samples with rAAV9 in solution prior to adding to the plate-bound rAAV9. The confirmatory assay conditions were optimal as shown by the high level of ELISA signal inhibition (96%) of the mouse monoclonal ADK9 positive control. Various levels of inhibition were seen for the different serum sample lots (50-72% range), suggesting that assay conditions might also be optimal for differentiating antibodies of various specificities. It is to be noted that we used the pan-isotype anti-human κ and λ constant region detection antibodies in the CL ELISA for the reason that early testing using an antihuman IgG detection antibody resulted in at least five out of 12 normal human serum samples showing relatively lower or less than background signals compared with anti-human κ and λ detection antibodies (FIG. 12).

Since gene therapeutic studies have historically employed colorimetric ELISAs for the detection of AAV antibodies, we deemed it important to do head-to-head comparisons between the two methods (chemiluminescent vs. colorimetric). In terms of signal-to-noise ratio (S/N), chemiluminescent (CL) ELISA was clearly superior colorimetric ELISA, as described in the Results section. Although CL protein ELISAs have been used for the detection of antibodies, to the best of our knowledge, this is the first report of the application of the CL ELISA for the detection of anti-AAV antibodies. It is also the first report of a confirmatory or specificity tier to anti-AAV antibody detection.

One hundred serum samples from patients with heart disease were analyzed for pre-existing AAV9 antibodies with the intent of correlating the total antibody data set with the cell-based neutralizing antibody data. Prior to the correlative analysis, we ensured that the two capsids were similar to one another with respect to antibody reactivity when probed with normal human serum samples or the mouse ADK9 monoclonal control. Evaluation of the total antibody and neutralizing antibody data for the 100 heart disease patient serum samples showed a significant negative correlation between the total antibody and neutralizing antibody data sets, indicating that most of the total antibodies detected in the CL ELISA had neutralizing properties. A similar correlative analysis between the neutralizing antibody data and the confirmatory ELISA data yielded a lower negative coefficient, but still showed a strong significance level. Due to the strong correlation observed in this study, the total and/or confirmatory antibody ELISAs are viable alternatives to the cell-based neutralizing antibody assay for screening and exclusion of subjects for rAAV9-based gene therapeutics.

Despite the differences in overlap of a few individual serum samples, the total and confirmatory antibody ELISAs represent an easier and quicker alternative to the cell-based neutralizing antibody assay since they capture most of the neutralizing antibody-positive population. In addition, the CL ELISAs have the added advantage of identifying antibodies that may neutralize by mechanisms that are independent of receptor-binding and entry. Given the high percentage of individuals who tested positive for anti-AAV9 antibodies in both formats (neutralizing antibody and confirmatory total antibody) and the anticipated need to screen a high number of patient samples for study recruitment, the advantages gained in terms of speed and low variability are higher. In the event that sufficient drug (transgene encapsulating viral capsid) is unavailable for the competitive inhibition portion of the assay, the total antibody assay with a cut-off of ≥700 units presents a viable alternative for subject screening and exclusion. The total antibody ELISA may be developed further to incorporate relative quantitation using purified human IgG, and a cut-off may be established based on weight over volume antibody levels.

While several studies in the past have addressed whether there might be a connection between antibody titers detected in ELISAs (binding antibodies) and neutralizing antibody titers measured in cell-based assay, none taught the substitution of cell-based assays with ELISA methods. Moreover, these studies used the colorimetric method of detection in the ELISAs and a variety of reporters in the cell-based neutralization assays including β-galactosidase, AAV replication proteins and luciferase to detect antibodies to AAV1, AAV2, AAV9 and other AAV serotypes. Two of these studies showed a poor correlation between the two assays for AAV2 antibodies (Chirmule et al., 1999; Erles et al., 1999). While one study that examined AAV1 titers in 51 healthy donor sera indicated that there might be a correlation between IgG titers in ELISA and neutralizing titers in that particular instance (Veron et al., 2012), another study assessed correlation in AAV9 ELISA and neutralizing antibody titers in 100 healthy human donor samples and reported that most anti-AAV9 IgG titers were non-neutralizing in nature (Thwaite et al., 2015). We have demonstrated a strong correlation between total ELISA antibodies and neutralizing antibodies for AAV9 and AAV2; the increased sensitivity of the CL method and the fact that we used the pan-isotype anti-human κ and λ constant region detection antibodies in the ELISA may have helped. We tested an anti-human IgG detection antibody early during method development and noted that at least five out of 12 normal human serum samples showed relatively lower or less than background signals compared with anti-human κ and λ detection antibodies (FIG. 12).

In summary, we have developed a highly sensitive chemiluminescent ELISA for the detection of anti-AAV9 antibodies and demonstrated a significant correlation with AAV9 neutralizing titers. This allows us to use the AAV9 ELISA in place of the cell-based neutralizing antibody assay for patient screening and exclusion in clinical trials and treatment of patients with FDA-approved AAV9 modalities. We have also built in a confirmatory tier to the AAV9 ELISA that facilitates a second-tier of screening. This is the first such report for the detection of AAV antibodies in a chemiluminescent method that also assesses specificity. Combined with titration, this assay can also be used to identify anti-drug antibodies (ADA) generated in response to AAV9-based gene therapeutics in a three-tier screen, confirmatory and titer approach where the cut-offs are set based on treatment-naive subjects.

The foregoing description of the specific embodiments fully reveals the general nature of the disclosure that others can, by applying knowledge within the skill of the art, readily modify and/or adapt the specific embodiments for various applications, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance overall.

Other embodiments of the disclosure will be apparent to those skilled in the art from consideration of the specification and practice of the present disclosure. It is intended that the specification and examples be considered as exemplary only, with a true scope and spirit of the disclosure being indicated by the following claims.

The disclosures of all publications, patents, and patent applications referenced herein are incorporated by reference in their entirety to the same extent as if the disclosure of each individual publication, patent or patent application was specifically and individually indicated to be incorporated by reference in its entirety.

What is claimed is:

1. A method of treating a disease in a subject in need of an AAV therapy, comprising administering to the subject the AAV therapy, wherein prior to the AAV therapy the subject is identified as having a low titer of an anti-AAV antibody in a biological sample obtained from the subject, wherein the low titer of the anti-AAV antibody is a titer of which the biological sample emits less than about 700 chemiluminescence units in a chemiluminescence enzyme-linked immunosorbent assay (ELISA).

2. A method of treating a disease in a subject in need of an AAV therapy, comprising (1) measuring the titer of an anti-AAV antibody in a biological sample obtained from the subject, wherein the biological sample emits less than about 700 chemiluminescence units in a chemiluminescence ELISA and (2) administering to the subject the AAV therapy.

3. The method of claim 1, wherein the disease is in the heart, liver, lungs, eyes, blood, nervous system, lymphatic system, muscle, stem cells or any combination thereof.

4. The method of claim 1, wherein:
   (a) the AAV therapy comprises a therapy with an AAV comprising AAV type 1, AAV type 2, AAV type 3A, AAV type 3B, AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any combination thereof; or
   (b) the anti-AAV antibody comprises an antibody specifically binds to AAV type 1, AAV type 2, AAV type 3A, AAV type 3B, AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, or shrimp AAV; or
   (c) both (a) and (b).

5. The method of claim 1, wherein the biological sample comprises a serum sample, a blood sample, or a combination thereof.

6. The method of claim 1, wherein the biological sample is diluted by at least about 1:2.

7. The method of claim 1, wherein the low titer of the anti-AAV antibody comprises a low titer of neutralizing anti-AAV antibodies.

8. The method of claim 1, wherein the AAV therapy comprises an AAV comprising a gene of interest.

9. The method of claim 8, wherein the gene of interest encodes a biologically active polypeptide.

10. The method of claim 8, wherein the AAV further comprises a regulatory sequence.

11. The method of claim 10, wherein the regulatory sequence comprises a tissue specific promoter.

12. The method of claim 11, wherein the tissue specific promoter drives expression of the gene of interest in a tissue comprising heart, liver, lungs, eyes, nervous system, lymphatic system, or muscle.

* * * * *